US 10,441,371 B2

United States Patent
Hendrick et al.

(10) Patent No.: US 10,441,371 B2
(45) Date of Patent: Oct. 15, 2019

(54) CONCENTRIC TUBE ROBOT

(71) Applicant: Vanderbilt University, Nashville, OH (US)

(72) Inventors: Richard J. Hendrick, Nashville, TN (US); Robert J. Webster, III, Nashville, TN (US); S. Duke Herrell, Nashville, TN (US); Philip J. Swaney, Nashville, TN (US); Ray Lathrop, Indianapolis, IN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 293 days.

(21) Appl. No.: 15/283,775

(22) Filed: Oct. 3, 2016

(65) Prior Publication Data
US 2017/0095299 A1   Apr. 6, 2017

Related U.S. Application Data
(60) Provisional application No. 62/236,187, filed on Oct. 2, 2015.

(51) Int. Cl.
*A61B 34/30* (2016.01)
*A61B 1/00* (2006.01)
(Continued)

(52) U.S. Cl.
CPC .......... *A61B 34/30* (2016.02); *A61B 1/00039* (2013.01); *A61B 1/00087* (2013.01);
(Continued)

(58) Field of Classification Search
CPC ............ A61B 1/00039; A61B 1/00087; A61B 1/00133; A61B 1/05; A61B 17/00234;
(Continued)

(56) References Cited

U.S. PATENT DOCUMENTS 5,704,892 A * 1/1998 Adair ................. A61B 1/00073
600/121
6,325,808 B1   12/2001 Bernard et al.
(Continued)

FOREIGN PATENT DOCUMENTS

WO       2014129672 A1   8/2014

OTHER PUBLICATIONS

International Search Report and Written Opinion for corresponding PCT/US2016/055137, dated Jan. 17, 2017, pp. 1-13.

*Primary Examiner* — John P Leubecker
*Assistant Examiner* — Shankar Raj Ghimire
(74) *Attorney, Agent, or Firm* — Tarolli, Sundheim, Covell & Tummino LLP

(57) ABSTRACT

A robotic surgical apparatus includes at least two tubes having a nested, concentric configuration with an inner tube positioned in an outer tube. The tubes are configured to deliver surgical therapy. A first tube carrier connected to the outer tube and a second tube carrier connected to the inner tube. The first tube carrier and its associated outer tube and the second tube carrier and its associated inner tube form a robotic arm assembly. An actuator for actuating the robotic arm assembly is configured to receive the robotic arm assembly via a tube insertion interface into which the robotic arm assembly can be inserted.

24 Claims, 19 Drawing Sheets

(51) Int. Cl.
*A61B 1/05* (2006.01)
*A61B 17/00* (2006.01)
*A61B 34/00* (2016.01)

(52) U.S. Cl.
CPC ...... *A61B 1/00101* (2013.01); *A61B 1/00133* (2013.01); *A61B 1/05* (2013.01); *A61B 17/00234* (2013.01); *A61B 34/72* (2016.02); *A61B 2017/00296* (2013.01); *A61B 2017/00318* (2013.01); *A61B 2017/00345* (2013.01); *A61B 2034/301* (2016.02); *A61B 2034/302* (2016.02); *A61B 2034/742* (2016.02)

(58) Field of Classification Search
CPC ........... A61B 2017/00296; A61B 2017/00318; A61B 2017/00345; A61B 2017/00991; A61B 2017/3443; A61B 2017/3447; A61B 2034/301; A61B 2034/302; A61B 2034/303; A61B 2034/742; A61B 34/30; A61B 34/72
See application file for complete search history.

(56) References Cited

U.S. PATENT DOCUMENTS

| | | | |
|---|---|---|---|
| 8,394,129 B2 * | 3/2013 | Morgenstern Lopez | A61B 17/1757 606/279 |
| 9,089,256 B2 * | 7/2015 | Tognaccini | A61B 1/00183 |
| 9,492,927 B2 * | 11/2016 | Diolaiti | B25J 9/1689 |
| 2007/0197896 A1 | 8/2007 | Moll et al. | |
| 2007/0287992 A1 * | 12/2007 | Diolaiti | G05B 19/19 606/1 |
| 2008/0051631 A1 * | 2/2008 | Dejima | A61B 1/0052 600/114 |
| 2008/0064921 A1 * | 3/2008 | Larkin | A61B 1/00087 600/104 |
| 2008/0071288 A1 | 3/2008 | Larkin et al. | |
| 2008/0154389 A1 * | 6/2008 | Smith | A61B 5/06 700/24 |
| 2010/0268241 A1 * | 10/2010 | Flom | A61B 17/3421 606/104 |
| 2010/0274087 A1 * | 10/2010 | Diolaiti | A61B 90/37 600/118 |
| 2011/0071508 A1 * | 3/2011 | Duval | A61B 1/00087 606/1 |
| 2012/0041263 A1 * | 2/2012 | Sholev | A61B 1/00149 600/118 |
| 2012/0080503 A1 * | 4/2012 | Woodard, Jr. | A61B 90/92 227/181.1 |
| 2013/0123802 A1 * | 5/2013 | Comber | A61B 34/30 606/130 |
| 2014/0005640 A1 * | 1/2014 | Shelton, IV | A61B 34/37 606/1 |
| 2014/0005680 A1 * | 1/2014 | Shelton, IV | A61B 18/1445 606/130 |
| 2014/0005708 A1 * | 1/2014 | Shelton, IV | A61B 17/07207 606/170 |
| 2014/0005718 A1 * | 1/2014 | Shelton, IV | A61B 17/07207 606/205 |
| 2014/0025089 A1 * | 1/2014 | Sholev | A61B 17/29 606/130 |
| 2014/0276949 A1 * | 9/2014 | Staunton | F16J 15/3256 606/130 |
| 2014/0277334 A1 * | 9/2014 | Yu | A61B 34/30 623/1.11 |
| 2015/0066022 A1 * | 3/2015 | Shelton, IV | A61B 18/082 606/41 |
| 2015/0080907 A1 | 3/2015 | Herrell et al. | |
| 2015/0223832 A1 * | 8/2015 | Swaney | A61B 17/3421 606/130 |
| 2016/0067450 A1 * | 3/2016 | Kowshik | A61M 25/0138 604/95.04 |
| 2016/0206347 A1 * | 7/2016 | Bar | A61M 29/00 |
| 2017/0273703 A1 * | 9/2017 | Ding | A61B 17/2909 |
| 2017/0367782 A1 * | 12/2017 | Schuh | A61B 1/00149 |

\* cited by examiner

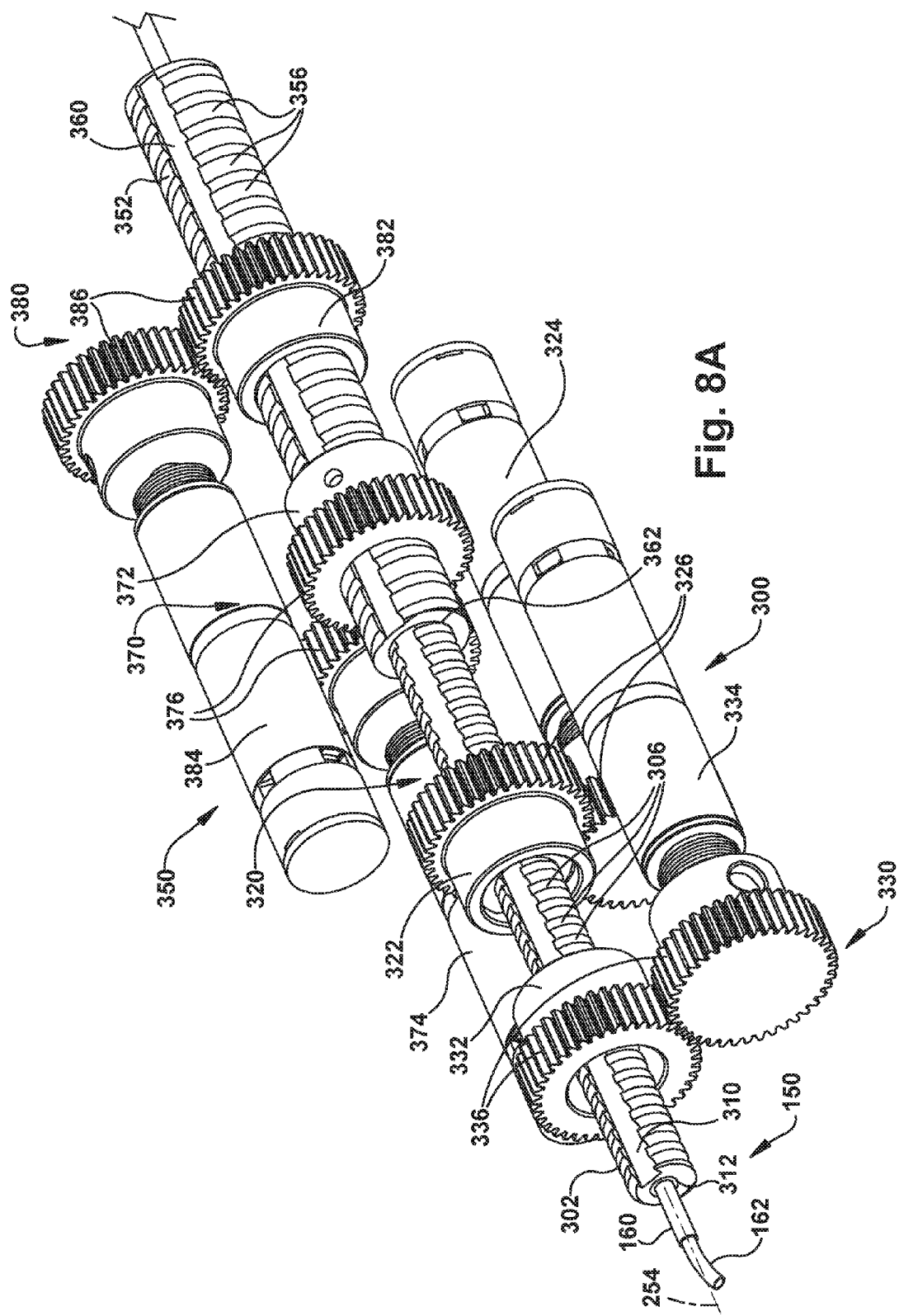

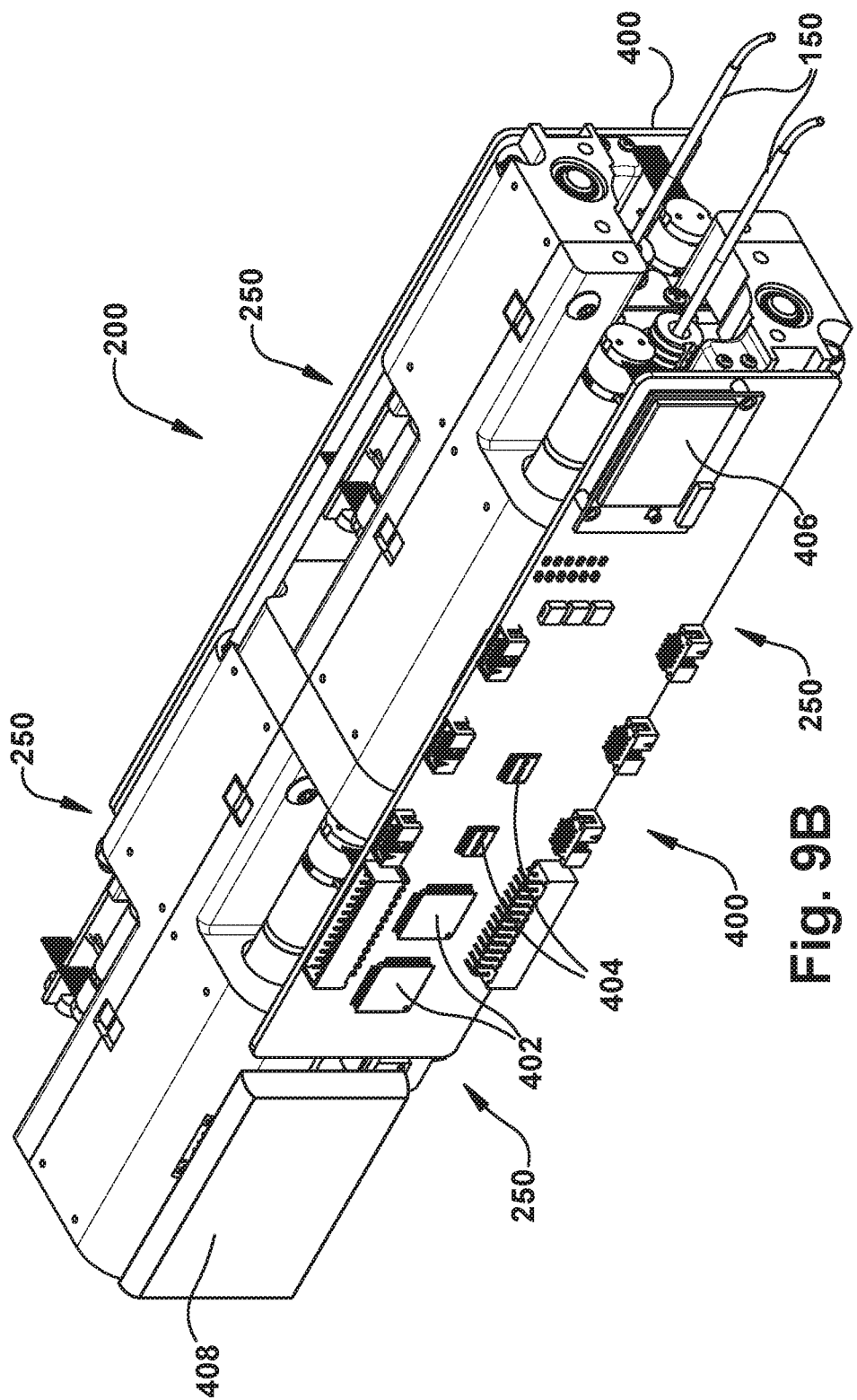

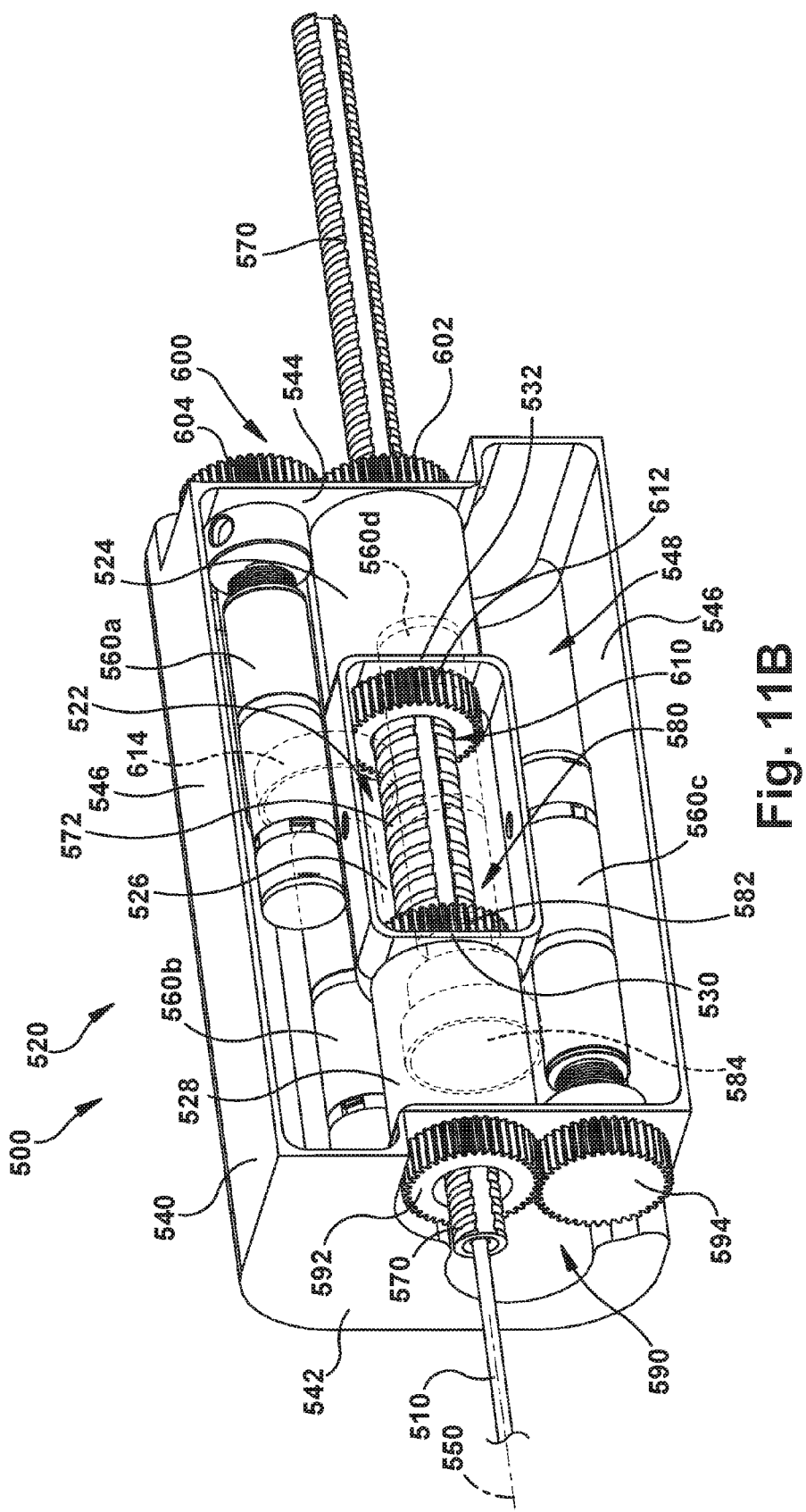

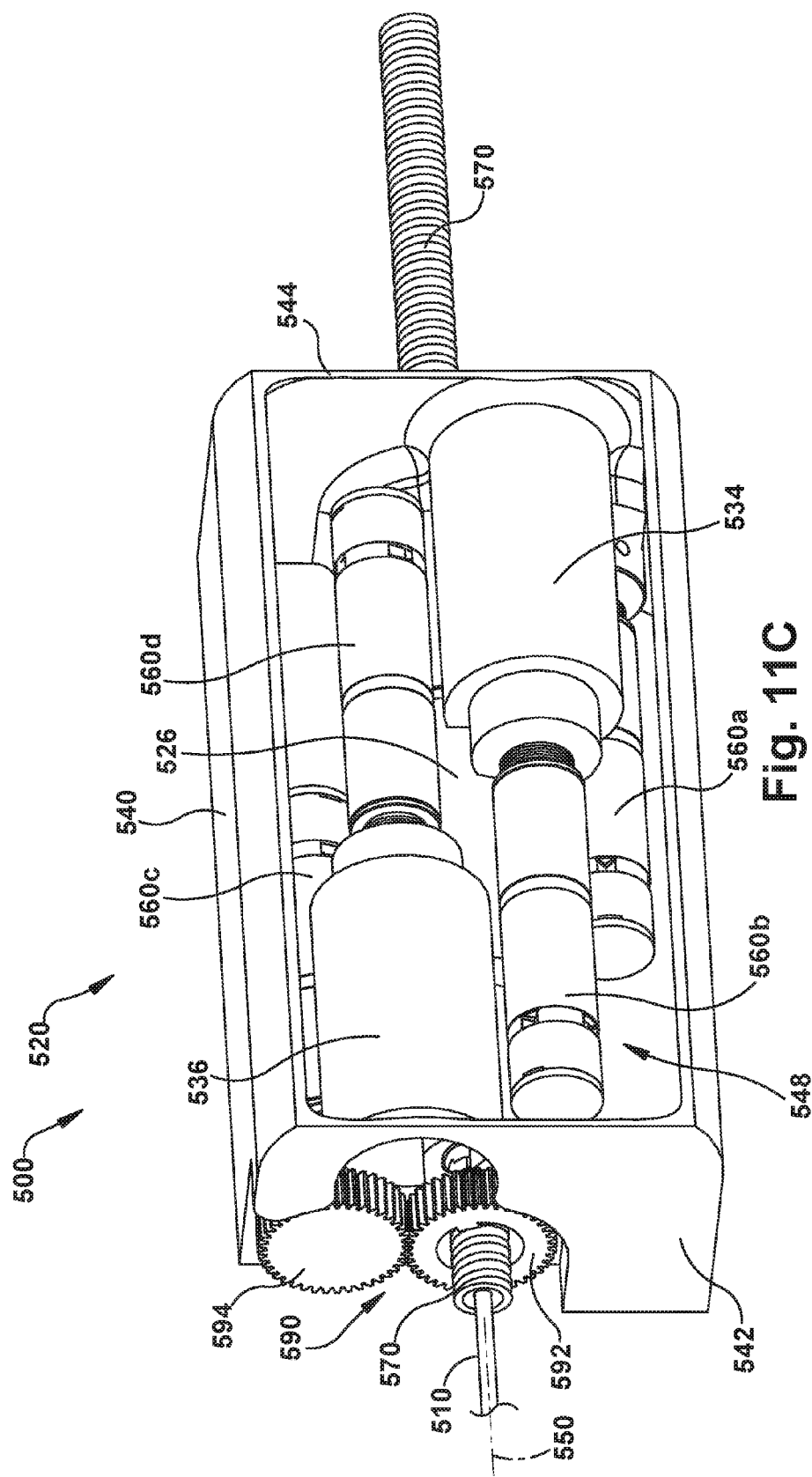

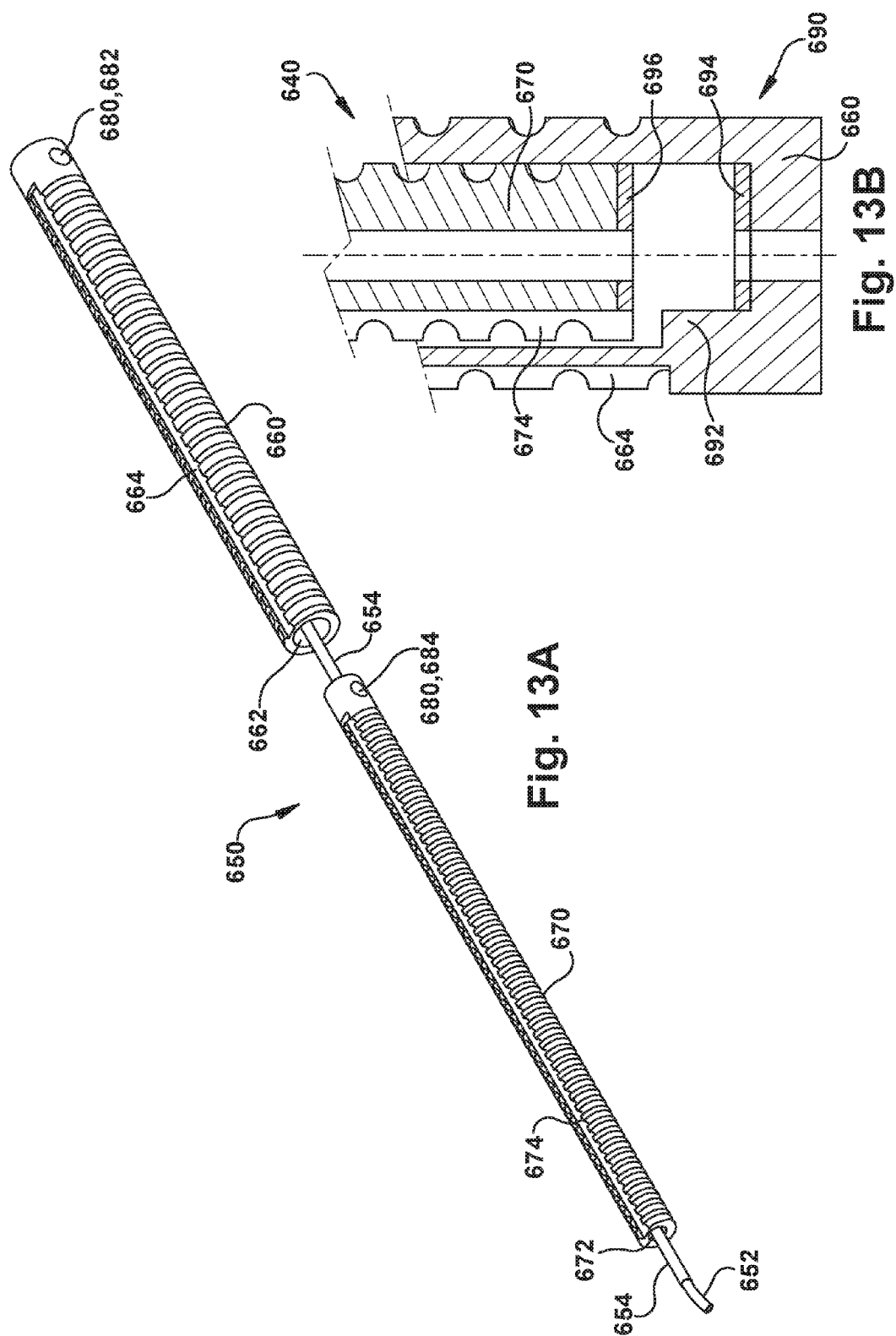

CONCENTRIC TUBE ROBOT

RELATED APPLICATIONS

This application claims the benefit of U.S. Provisional Application Ser. No. 62/236,187, filed Oct. 2, 2015. The subject matter of this provisional application is hereby incorporated by reference in its entirety.

GOVERNMENT RIGHTS

This work was funded in part by Endonasal NSF Career Grant No. NSF IIS 1054331 and NIH R01 EB017467. The U.S. Government may have certain rights to the invention.

FIELD OF THE INVENTION

The present invention relates to surgical tools for performing surgical operations. More specifically, the present invention relates to small diameter surgical tools for navigating the patient's anatomy in order to deliver therapy to a target location in the patient's body. In particular, the present invention relates to robotic devices used to manipulate small diameter concentric tubes used to deliver microsurgical tools to target locations in the body.

BACKGROUND

The shift toward minimally invasive surgical techniques presents a growing need for robotic or remotely controlled hand-operated surgical tools. These small-diameter surgical tools can be used to access a surgical site in a minimally invasive manner, while retaining the ability to allow the surgeon to manipulate the target tissue in order to perform a surgical procedure.

Currently, these procedures are implemented using small-diameter surgical tools, such as small diameter tubular probes, such as endoscopes, that are used to deliver a tool or end effector tailored to the specific procedure being performed. Since, however, these probes are rigid in construction, maneuvering the distal tip where the tool is located can become problematic. This is because small movements of the distally located tool can necessitate larger movement of more proximally located portions of the probe. These larger movements can be problematic because the anatomy simply will not permit the required movement of the probe, and because the probe can engage and potentially damage surrounding anatomical structures such as organs, vessels, nerves, muscles, bones, etc.

Accordingly, it is desirable to provide a system or apparatus that is capable of delivering surgical tools to a surgical target location and of permitting maneuvering of those tools without requiring that the entire delivery structure be manipulated as a whole. Most existing small diameter surgical tools do not include bendable or dexterous tips and thus cannot navigate the sharp corners encountered in surgery, such as those at the skull base, in the middle ear, and in the ankle. Moreover, dexterity driven tasks, such as tissue resection and suturing, can be difficult to perform without a bendable tip, especially through the small openings characteristic of natural orifice or percutaneous procedures.

Recent advances in surgical robotics are enabling less invasive access to the human body through natural orifices. Transoral surgery has been an approach of substantial recent interest, perhaps since the mouth is the largest natural orifice. Many in the surgical community have focused on using Intuitive Surgical, Inc.'s da Vinci™ Surgical System robot for this purpose, while engineering interest has focused on custom designed robot solutions. There has been a recent progression in the surgical robotics community toward designing robots to work through ever smaller orifices. Numerous systems have been designed for colorectal inspection and surgery. Recently, teleoperated and/or cooperative systems have been developed for ear surgery, endonasal surgery, and transurethral bladder surgery. Yet despite the relatively small diameter of the urethra, it is also interesting to note that transurethral surgery was actually one of the earliest surgical robotics applications.

Benign prostatic hyperplasia (BPH), or enlargement of the prostate, is the most prevalent symptomatic disease in men, occurring in 8% of men in their 30s, 50% in their 50s, and 90% in their 80s. BPH occurs when the prostate grows large enough that it restricts the flow of urine through the urethra, which passes through the prostate. The goal of a surgical intervention for BPH is to remove prostate tissue surrounding the urethra and thereby enable normal urine flow to resume. Transurethral resection of the prostate (TURP) is the current standard surgical approach for BPH. It is accomplished endoscopically, through the urethra, and prostate tissue is removed in pieces by either sharp dissection or electrocautery. Although the approach to the prostate is minimally invasive, the tools used to remove tissue can cause substantial bleeding (potentially requiring transfusion), long catheterization time, urethral narrowing, and bladder neck narrowing.

Holmium Laser Enucleation of the Prostate (HoLEP) is another surgical procedure for treating BPH. HoLEP can alleviate many of these concerns, since the Holmium laser provides an ideal combination of cutting and coagulation. HoLEP enables dissection without significant thermal spread (making HoLEP safer than electrocautery for nearby structures such as nerves), and without substantial blood loss. The reduction in morbidity in HoLEP compared to TURP has been corroborated in a number of clinical studies. These show that HoLEP reduces average catheterization time (2 days to 1 day), hospital stay (3 days to 2 days), and blood loss (eliminates the need for transfusions). The improvement in outcomes is sufficiently compelling that HoLEP is now generally viewed in the urology community as the superior treatment.

In spite of this, HoLEP adoption has been slow, and it is currently only conducted in relatively few institutions in the USA compared to TURP, which was conducted approximately 50,000 times in the United States in 2005. The best explanation for why HoLEP has not been more widely adopted is that it is extremely challenging for the surgeon. The challenge is brought about due to the fact that the laser proceeds straight out of the endoscope and can only be aimed by moving the entire endoscope. Since the endoscope must pass through a great deal of soft tissue on the way to the prostate, its maneuverability is limited. Large forces are required to aim the endoscope and the only way to physically manipulate tissue near its tip is to use the tip of the endoscope itself. It is challenging and physically demanding for surgeons to attempt to accurately aim the laser using the endoscope while simultaneously applying large forces to the same endoscope to deform the tissue.

SUMMARY

The invention relates to a robotic system, method, and apparatus for performing endoscopic surgery. The endoscopic approach can implement a rigid or flexible endoscope to access a target surgical site through a port in the body.

These ports can be natural orifices (e.g., mouth, nose, ears, rectum, urethra) or incisions (e.g., chest, abdomen, head). In one implementation, the invention relates to a robotic surgical system that deploys two or more robotic concentric tube manipulators through an endoscope.

The robotic surgical system can be implemented to perform a wide variety of surgical procedures. In one implementation, the robotic surgical system is used to perform transurethral surgery that focuses on the prostate. In this implementation, the robotic surgical system is used to perform a transurethral Holmium Laser Enucleation of the Prostate (HoLEP), which is useful in the management of Benign Prostatic Hyperplasia (BPH). According to one aspect, the robot is adapted for both manual and robotic operation.

According to this aspect, a robotic system deploys one or more concentric tube manipulators, each of which includes a tool adapted for the particular surgical procedure for which the system is being used. These tools can, for example, include HoLEP laser fibers, grippers, surgical lasers, graspers, retractors, scissors, imaging tips (e.g., endomicroscopy, optical coherence tomography (OCT), spectroscopy), cauterization tips, ablation tips, wrists (for dexterity), curettes, morcelators, knives/scalpels, cameras, irrigation ports, and suction ports. Additional surgical tools can, of course, be envisioned.

According to one aspect, the concentric tube manipulators can be delivered through a conventional endoscope or endoscope tube that is fit with a video camera and an illumination source for facilitating remote viewing. Through this system, the surgeon can manually manipulate the endoscope to place its distal end at a desired location relative to the target. Once positioned, the surgeon can use the concentric tube manipulators to perform the surgical procedure. For example, in a urological implementation, the surgeon could insert the endoscope transurethrally and manipulate the endoscope to position its distal tip at a desired location relative to the prostate. The concentric tube manipulators can be operated robotically, carrying a HoLEP laser and a gripper that allows for manipulating tissue, exposing areas for laser dissection, and removing dissected tissues from the patient's body.

Through this operation, the surgeon can control gross motions of the endoscope manually in the usual accustomed manner, while fine motions of the concentric tube manipulators at the endoscope tip are accomplished via controller interface devices, such as thumb joysticks and finger triggers located near the surgeon's hands. The surgeon can view the endoscope image on a screen, which can be positioned on the back of the robot unit or on a display screen in the operating room.

Advantageously, the endoscope that passes into the patient can be of the same diameter as that currently used for various clinical procedures, such as HoLEP procedures. These diameters can, however, be smaller or larger, as the procedure dictates.

According to one aspect, a robotic surgical apparatus includes at least two tubes having a nested, concentric configuration with an inner tube positioned in an outer tube. The tubes are configured to deliver surgical therapy. A first tube carrier connected to the outer tube and a second tube carrier connected to the inner tube. The first tube carrier and its associated outer tube and the second tube carrier and its associated inner tube form a robotic arm assembly. An actuator for actuating the robotic arm assembly is configured to receive the robotic arm assembly via a tube insertion interface into which the robotic arm assembly can be inserted.

According to another aspect, alone or in combination with any other aspect, the tube insertion port can be positioned on a rear portion of the actuator. The actuator can have a pass-through configuration in which the robotic arm passes axially through the actuator and exits a front portion of the actuator.

According to another aspect, alone or in combination with any other aspect, the robotic surgical apparatus can include an endoscope having a tip configured to be positioned at a surgical site in the patient. The apparatus can be operable to deliver the robotic arm through the endoscope to the surgical site.

According to another aspect, alone or in combination with any other aspect, the robotic surgical apparatus can include a quick release mechanism for detaching the endoscope.

According to another aspect, alone or in combination with any other aspect, the endoscope can include a camera having a viewpoint that is angled relative to a longitudinal axis of the endoscope. The viewpoint can be at least one of rotatable, translatable, and angularly adjustable relative to the endoscope tip in order to adjust the field of view.

According to another aspect, alone or in combination with any other aspect, the endoscope can include a distally located exit port through which the robotic arm extends. The exit port can be translatable relative to the endoscope tip in order to adjust the exit location of the robotic arm.

According to another aspect, alone or in combination with any other aspect, the apparatus can impart motion to two robotic arm assemblies. The endoscope can include a distally located exit port insert through which the robotic arms extend. The exit port insert can be translatable relative to the endoscope tip individually in order to adjust the exit locations of the robotic arms individually.

According to another aspect, alone or in combination with any other aspect, the endoscope can include a distally located exit port through which the robotic arm extends. The exit port can have a curved configuration that permits the robotic arm to exit the exit port at an angle or along a curved trajectory relative to the endoscope axis.

According to another aspect, alone or in combination with any other aspect, the first tube carrier can include a first lead screw connected coaxially with an end portion of the outer tube. The second tube carrier can include a second lead screw connected coaxially with an end portion of the inner tube. The robotic surgical apparatus can further include a first lead nut through which the first lead screw extends and which has threads that mate with threads of the first lead screw such that rotation of the first lead nut imparts translational movement of the first lead screw. The robotic surgical apparatus can also include a second lead nut through which the second lead screw extends and which has threads that mate with threads of the second lead screw such that rotation of the second lead nut imparts translational movement of the second lead screw. The robotic surgical apparatus can also include a first collar through which the first lead screw extends, the first collar and first lead screw comprising a keyed mechanism configured such that rotation of the first collar imparts rotational movement of the first lead screw. The robotic surgical apparatus can further include a second collar through which the second lead screw extends, the second collar and second lead screw comprising a keyed mechanism configured such that rotation of the second collar imparts rotational movement of the second lead screw.

According to another aspect, alone or in combination with any other aspect, the lead screws, lead nuts, and collars can be aligned coaxially along a single axis.

According to another aspect, alone or in combination with any other aspect, the robotic surgical apparatus can include an electric motor corresponding to each of the lead nuts and each of the collars. The motors can be independently actuatable to impart rotation to the lead nuts and to the collars.

According to another aspect, alone or in combination with any other aspect, the robotic surgical apparatus can also include a control unit including one or more motor controllers for controlling operation of the electric motors, and a controller configured to communicate and control operation of the motor controllers. The controller can be configured to perform kinematic computations to transform user inputs into motor controller commands.

According to another aspect, alone or in combination with any other aspect, the robotic surgical apparatus can also include a controller for controlling operation of the electric motors to impart translation, rotation, or both translation and rotation to the lead screws and their associated tubes. To produce pure rotational movement of the lead screws, the controller can be programmed to operate the electric motors to impart rotation of both the lead nuts and the collars at the same absolute angular velocity.

According to another aspect, alone or in combination with any other aspect, the first and second tube carriers screws can be tubular, each including a longitudinally extending central channel. The first tube carrier can be dimensioned to fit within the central channel of the second tube carrier in a concentric and telescoping manner. The first and second tube carriers can be rotatable and translatable relative to each other.

According to another aspect, alone or in combination with any other aspect, the robotic arm assembly can include a retention mechanism for maintaining the relative positions of the first and second tube carriers during insertion of the robotic arm assembly into the actuator.

According to another aspect, alone or in combination with any other aspect, the retention mechanism comprises a spring loaded ball and detent mechanism or a magnetic mechanism.

According to another aspect, alone or in combination with any other aspect, the actuator can have a tube installation mode in which tube actuation components are positioned automatically to align with engagement features of the tube carriers when the robotic arm assembly is inserted through the tube insertion interface.

According to another aspect, alone or in combination with any other aspect, the actuator can be configured to enter the tube installation mode automatically in response to insertion of the robotic arm assembly.

According to another aspect, alone or in combination with any other aspect, the actuator can have a tube retraction mode in which the inner and outer tubes are retracted from the patient automatically. The apparatus can be configured to retract the inner and outer tubes along the same path along which the tubes were delivered into the patient.

According to another aspect, alone or in combination with any other aspect, the actuator can have a tube exchange mode in which the inner and outer tubes are retracted to a position where at least the inner tube can be removed from the actuator and replaced with a different inner tube.

According to another aspect, alone or in combination with any other aspect, the inner tube can have a distal tip configured to support surgical tools. The surgical tools can be delivered to the tip through an inner lumen of the inner tube. The tip of the inner tube and the surgical tool can include portions that cooperate to form a connection mechanism for connecting the surgical tool to the tip of the inner tube. The surgical tool can be manipulated to engage and disengage the connection mechanism remotely by manipulating a tool apparatus member that is connected to the tool and extends through the inner lumen of the inner tube.

According to another aspect, alone or in combination with any other aspect, the connection mechanism can include a threaded connection or a pin-and-slot locking mechanism.

According to another aspect, alone or in combination with any other aspect, the actuator can include a housing comprising an inner chamber and a tube channel that extends through the inner chamber. The tube channel can be isolated from the inner chamber. Motors for actuating the robotic arm assembly and electronic components associated with the motors can be housed in the inner housing. The robotic arm assembly can extend through the tube channel.

According to another aspect, alone or in combination with any other aspect, the motors and electronics can be sealed in the inner chamber. The seal of the inner chamber can be sufficiently gas-tight to permit the apparatus to be sterilized.

According to another aspect, alone or in combination with any other aspect, the robotic surgical apparatus can include sealed bearing structures through which motor shafts extend from the inner chamber into the tube channel. The sealed bearing structures can maintain the seal between the inner chamber and the tube channel to a level sufficient to permit sterilization of the actuator.

According to another aspect, alone or in combination with any other aspect, the actuator can include a disposable transmission assembly for receiving the robotic arm assemblies and imparting translational and rotational movement to the robotic arm assembly. The actuator can also include at least one motor and electronics pack that is connectable to the transmission assembly and is operable to provide motive force to the disposable transmission assembly for imparting the translational and rotational movement to the robotic arm assembly.

According to another aspect, alone or in combination with any other aspect, the motor and electronics pack can include controller components for controlling operation of the motors in order to control actuation of the robotic arm assemblies.

According to another aspect, alone or in combination with any other aspect, a robotic surgical apparatus can include a robotic arm including at least two tubes having a nested, concentric configuration with an inner tube positioned in an outer tube. The robotic arm can be configured to deliver surgical therapy. The robotic surgical apparatus can also include a first tube carrier connected to the outer tube of the robotic arm and a second tube carrier connected to the inner tube of the robotic arm. The tube carriers and the robotic arm form a robotic arm assembly. The robotic surgical apparatus can also include an actuator for actuating the robotic arm assembly and an endoscope connected to the actuator. The robotic arm can extend through the actuator and into the endoscope. The endoscope can include a distally located exit port through which the robotic arm can extend. The exit port can have a curved configuration that permits the robotic arm to exit the exit port along an angled or curved trajectory.

DRAWINGS

FIG. 8A is a perspective view illustrating the spatial relations and interactions of certain components of another example configuration of the robot apparatus.

FIGS. 9A and 9B are perspective views certain components of another example configuration of the robot apparatus.

FIGS. 11A-11D are perspective views illustrating another example configuration of the robot apparatus and certain portions thereof.

FIGS. 13A and 13B are perspective and sectional views, respectively, illustrating certain components of another example configuration of the robot apparatus.

DESCRIPTION

The Surgical System

Figure 1:
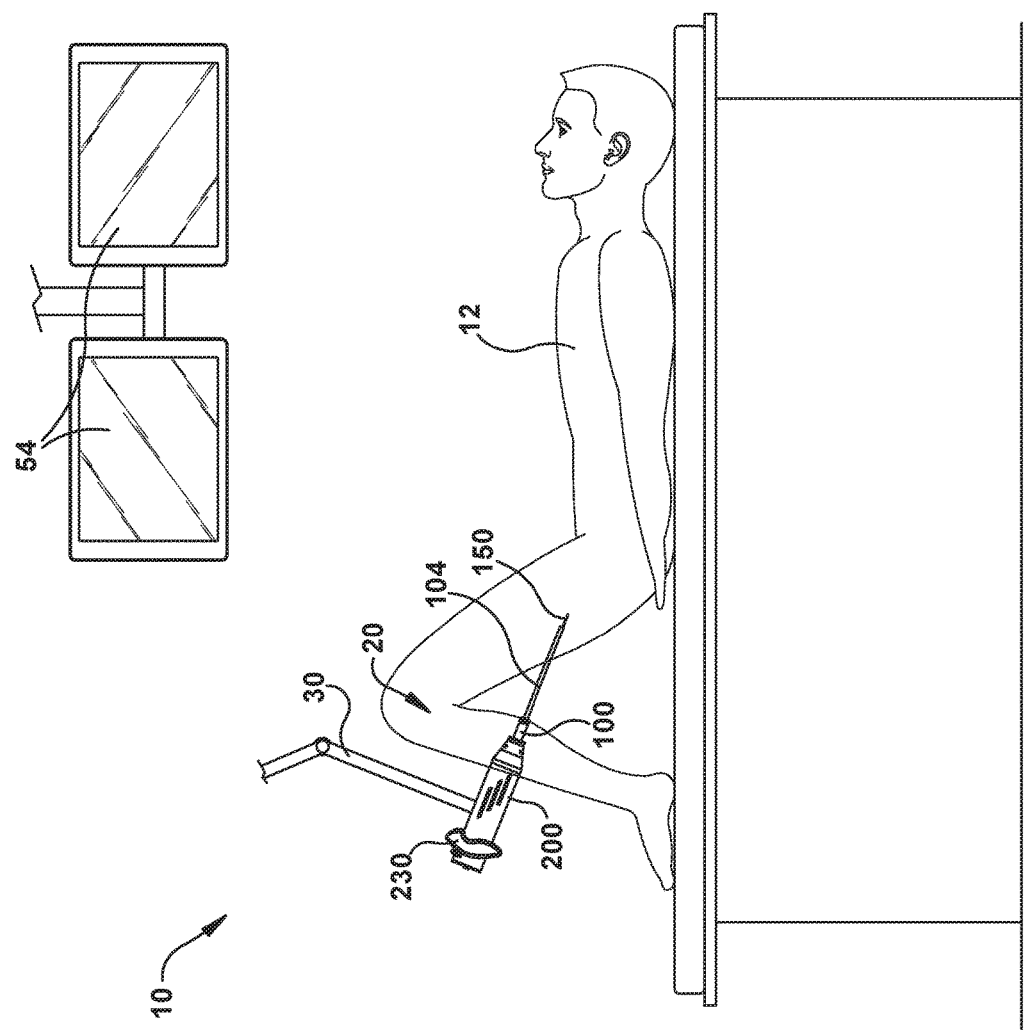
FIG. 1 illustrates a system including a robot apparatus for manipulating concentric tubes for delivering surgical tools, according to an example configuration.

FIG. 1 illustrates an operating room environment in which surgery can be performed. Referring to FIG. 1, a system 10 for performing surgery on a patient 12 includes a robotic apparatus 20, referred to herein as a "robot." The robot 20 includes an endoscope 100 through which one or more concentric tube robotic arms 150 extend. Concentric tube manipulators can also be referred to as "active cannulas" or "concentric tube robots." In this description, for simplicity, the concentric tube robotic arms 150 are also referred to as "robotic arms." Each of the robotic arms 150 carry at their distal end an end effector or tool (described in greater detail below). In this description, the robot 20 is illustrated and described as including two robotic arms 150. The robot 20 could, however, include a single robotic arm 150 or more than two robotic arms.

The robot 20 also includes an actuation unit 200 for manipulating the operation of the robotic arms 150 and the end effectors carried by the robotic arms. The actuation unit 200 includes control interface devices 230 that allow the user to maneuver the robot 20 relative to the patient 12 and also to control the operation of the robotic arms 150 and the end effectors they carry. The actuation unit 200 also includes a coupler 202 for receiving and coupling with the endoscope 100.

The robot 20 is supported on a support device, which is illustrated generally at 30. The support device 30 can include a counterbalance mechanism that compensates for or negates the effects of gravity so that the user (i.e., surgeon) can easily maneuver and position the robot 20. To achieve this, the support device 30 can be configured (e.g., counterbalanced) so as to negate all or a portion of the weight of the robot 20. The support device 30 can also have locking features that allow the user to fix the position of the robot 20 so that the user can focus on manipulating the robotic arms 150 via the control interface devices 230.

Control of the robot 20 can be implemented onboard the robot through the use of onboard components, processors, memory, video controllers, motor controllers, etc., off-board via external controllers and/or computers, or through a combination of onboard and off-board controls. Guidance of the robot 20 can be facilitated through the use of onboard video delivered via the endoscope 100, viewed on monitors 54 in the operating room, connected via wire or wirelessly. Additional imaging guidance systems, such as ultrasound systems, can also be used to aid the user in guiding the robot 20 in the patient 12.

Figure 2:
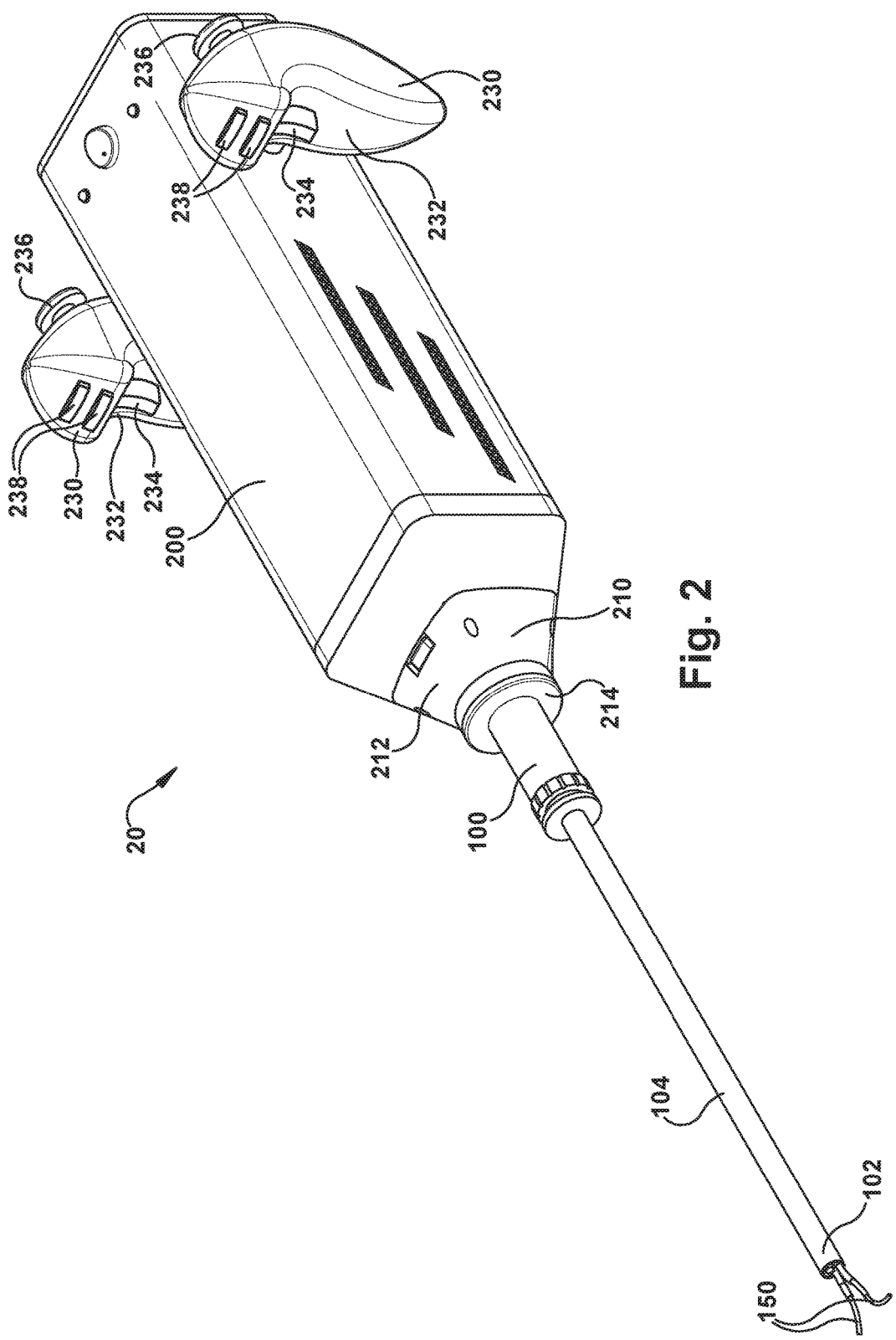
FIG. 2 is a perspective view illustrating an example configuration of the robot apparatus of FIG. 1.

The control interface devices 230 can have a variety of configurations. Referring to FIG. 2, in one example, the control interface devices can have a familiar, videogame-style configuration with an ergonomic handle 232, an index finger trigger 234, and a thumb actuated joystick 236. Additional control buttons, such as forward located index finger actuated buttons 238, can also be included. In one example control scheme, the joysticks 236 can be used to actuate 360 degree up/down, left/right motion of the tips of the robotic arms. The triggers 234 can be used to actuate the tools at the tips of the robotic arms 150. Maneuvering of the endoscope 100 itself can be performed manually by the surgeon, gripping the handles 232 and moving the robot 20, aided by the support device 30. Once the tip of the endoscope 100 is positioned at the worksite, the support device 30 can be locked in place and the surgeon can control the concentric tube robotic arms 150 to perform the surgical procedure.

As another alternative, the robot 20 can be controlled remotely. For example, the robot can be controlled from a console or workstation where control interface devices, such as the control interface devices 230, are mounted. The workstation can also include viewing monitors, camera controls, tool controls, and any other controls for operating the equipment associated with the surgical procedure. Advantageously, this can also allow the surgeon to perform the operation from a comfortable position, thus helping to prevent fatigue. Additionally, the workstation control implementation can provide uniformity in the layout of the controls so that the surgeon is provided a familiar control setup through which to operate.

Endoscope Design

Figure 3A:
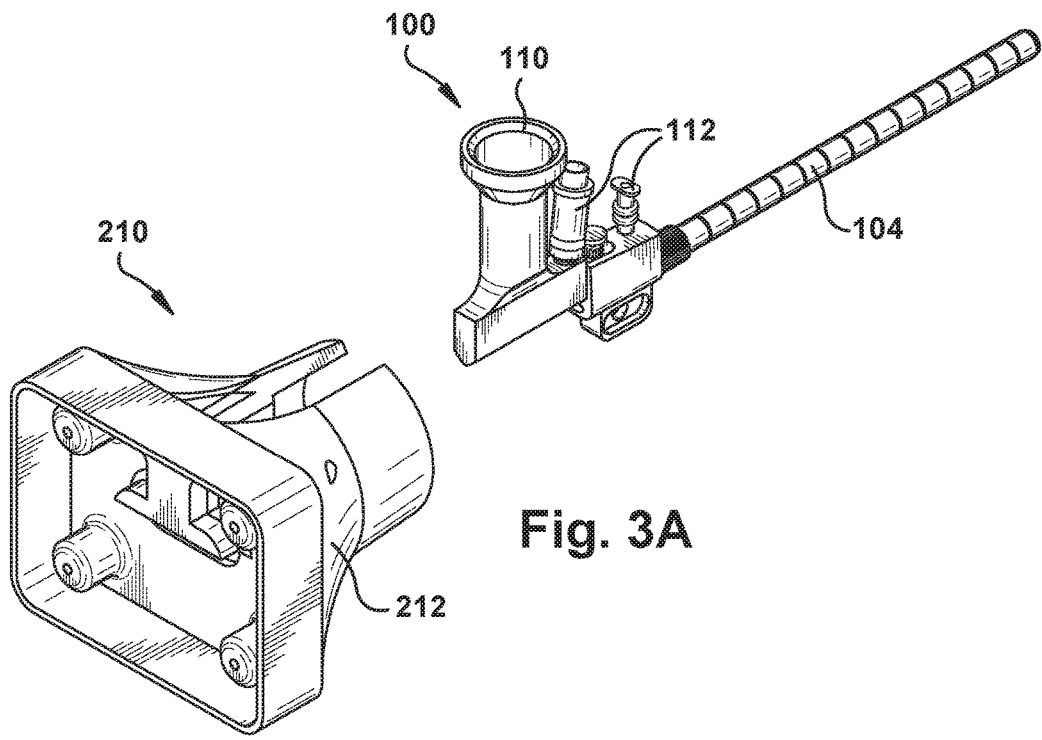
FIGS. 3A and 3B are perspective views of an example configuration of portions of the robot apparatus in different conditions.
Figure 3B:
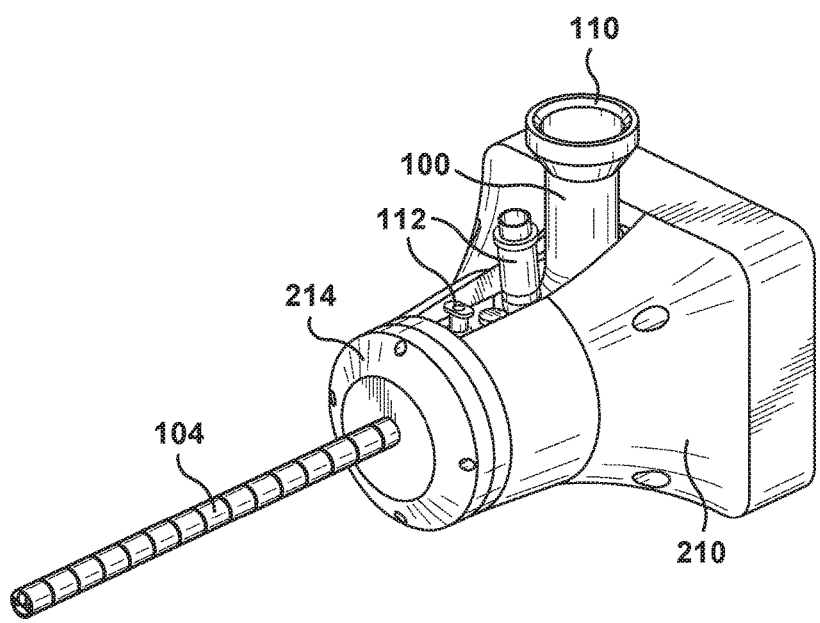

Referring to FIG. 2, the robotic arms 150 extend from the actuator 200 through the endoscope 100 and protrude from a distal end 102 of the endoscope probe/tube 104. The robotic arms 150 can be configured so that they can be retracted into the endoscope tube 104 while it is being maneuvered to the surgical site. The endoscope 100 can be of a design that is customized specifically to deliver the concentric tube robotic arms 150 (described in further detail below). Alternatively, the endoscope can be a conventional endoscope available commercially as an off-the-shelf device. An example of a specialized endoscope 100 is illustrated in FIG. 2. An example of a commercially available endoscope 100 is illustrated in FIGS. 3A and 3B.

As shown in FIG. 2, the robot 20 includes a coupling 210 for connecting the endoscope 100 to the actuator 200. As a representative example, one configuration for the coupling 210 is illustrated in FIGS. 3A and 3B. The coupling 210 includes a base 212 that connects to the actuator 200 and a cap 214 that connects to the base. The endoscope 100 is installed in the base 212, which is configured to receive, mate with and engage endoscope to provide strong, rigid support. The cap 214 is installed over the endoscope tube 104 and fixed to the base 212 so as to retain the endoscope 100 in the coupling 210. The cap 214 can be connected, for example, via a threaded connection in a screw-on fashion or via threaded fasteners.

The coupling 210 can have alternative configurations. For example, the coupling 210 can be configured to retain the connection of the endoscope via a releasable snap-in mechanism (not shown) in which the endoscope is retained, for example, by a spring biased latch that can be disengaged via pushbutton to release the endoscope. Note also that in FIGS. 3A and 3B, the coupling 210 is adapted to accommodate the use of the commercially available endoscope 100, which can include a camera port 110 and ports 112 for suction, irrigation, drug delivery, etc. To facilitate this, the base 212 of the coupling 210 can include an opening or slot 216 through which these components can extend.

Figure 4:
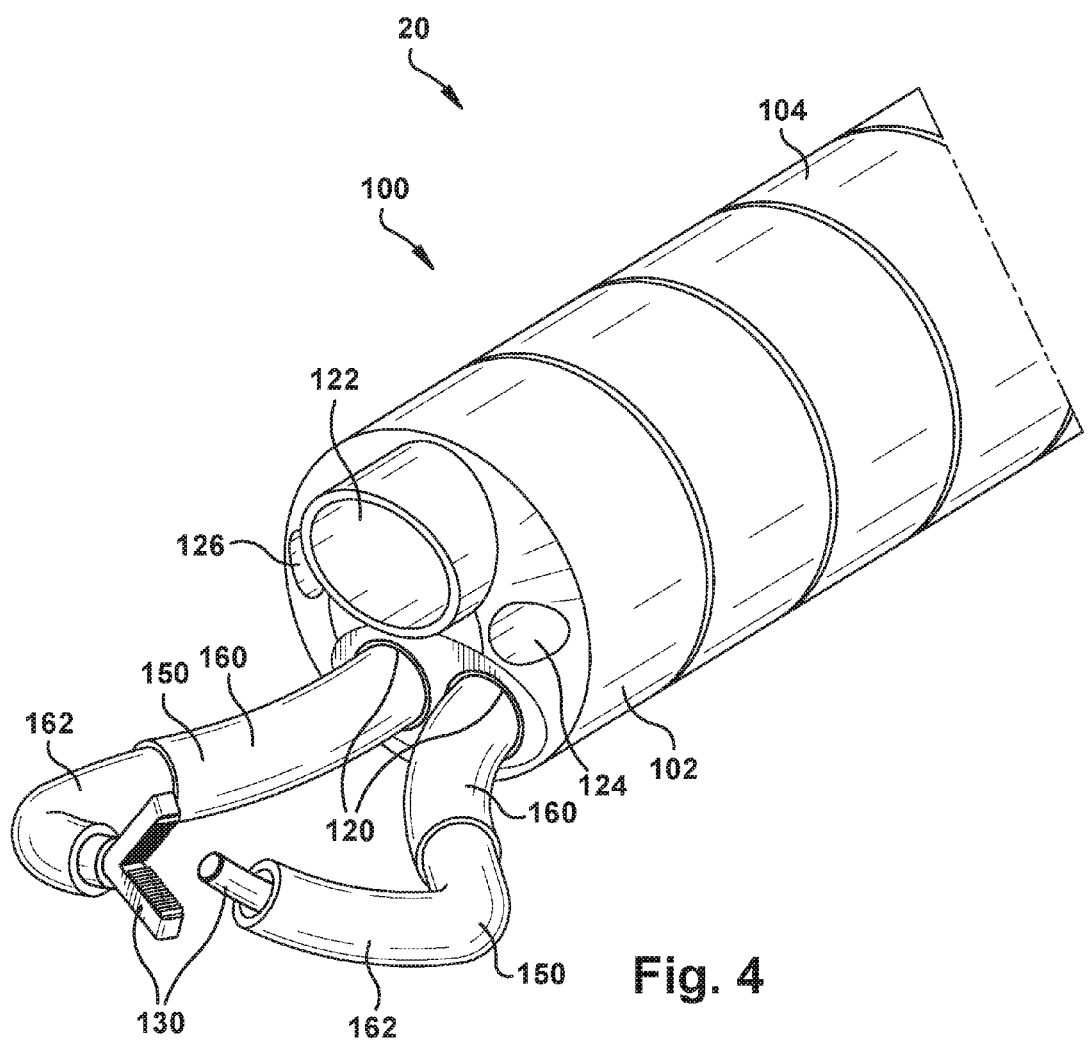
FIG. 4 is a magnified perspective view illustrating an example configuration of another portion of the robot apparatus.

One specific example of an endoscope 100 that is configured specifically for use with the concentric tube robotic arms 150 is illustrated in FIG. 4, which illustrates the distal end 102 of the endoscope tube 104. As shown in FIG. 4, the endoscope 100 can include exit ports 120 through which the robotic arms 150 extend. The endoscope 100 also includes a camera 122 and an illumination source 124, such as an LED. The endoscope can further include ports 126 for suction, irrigation, and drug delivery.

This description recognizes that the camera 122 can take many forms and, thus, the element through which the field-of-view is obtained can vary. For example, in the classic sense of a camera, the field-of-view can be obtained through a lens. Fiber-optic cameras, however, can obtain the field-of-view via an optical fiber. For this reason, in this description, reference is made to the "viewpoint" of the camera as obtaining the field-of-view so as to encompass all of these different possible image gathering structures.

The camera 122 can have a viewpoint that is angled so that the camera's field of view is directed toward the workspace accessed by the robotic arms 150 so that the surgical tools 130 employed by the robotic arms can be viewed during the procedure. In the example configuration of FIG. 4, the robotic arms 150 can be configured to perform HoLEP laser surgical operations. Thus, one robotic arm 150 can be fit with a tool 130 in the form of grippers for grasping and manipulating tissue and the other robotic arm can be fit with a tool 130 in the form of a HoLEP laser fiber element.

Figure 5A:
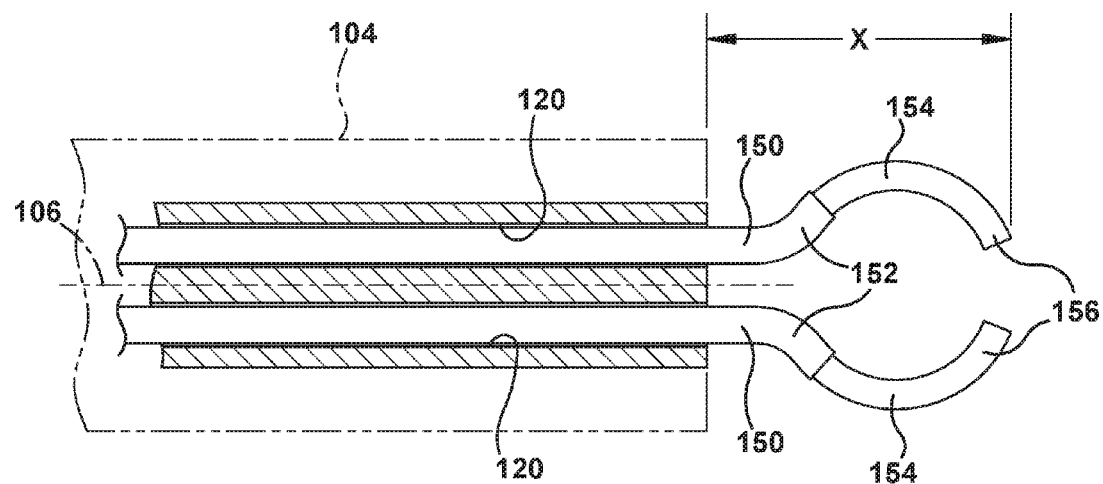
FIGS. 5A and 5B are magnified sectional views illustrating alternative example configurations of another portion of the robot apparatus.
Figure 5B:
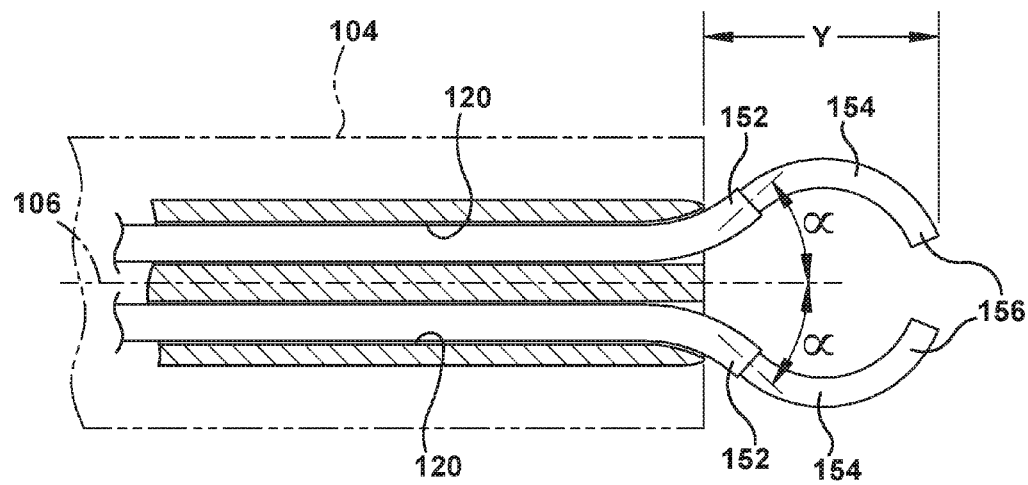

As shown in FIGS. 5A and 5B, the exit ports 120 can be configured to control or adjust the angle at which the concentric tube robotic arms 150 extend from the endoscope tube 104. In the example configuration of FIG. 5A, the exit ports 120 are straight ports directed parallel to the axis 106 of the endoscope tube 104. In this configuration of the exit ports 120, the robotic arms 150 exit the endoscope tube 104 at a trajectory that is parallel to the endoscope axis 106. From there, the robotic arms 150 extend along their respective curved trajectories.

In the example configuration of FIG. 5B, the exit ports 120 have curved ends that deviate from the endoscope axis 106. In this configuration of the exit ports 120, the robotic arms 150 exit the endoscope tube 104 at trajectories that are angled with respect to the endoscope axis 106, as indicated generally by the angles α in FIG. 5B. From there, the robotic arms 150 extend along their respective curved trajectories. The exit ports 120 could have alternative configurations for directing the robotic arms 150 along a desired trajectory or path. For example, the exit ports can extend along a helical or S-shaped path. In addition to helping direct the robotic arms along a desired path, the configurations of the exit ports 120 can also help navigate the robotic arms 150 to avoid other structures within the endoscope 100, such as wires, optical fibers, etc.

Advantageously, the angled exit ports can help adjust or move the position of the workspace relative to the distal end 102 of the endoscope tube 104. In FIGS. 5A and 5B, the inner tubes 154 extend from their respective outer tubes 152 along the same curved path. As shown in FIG. 5A, the straight exit ports 120 result in the tips 156 of the inner tubes 154 arrive at their illustrated positions at a distance, indicated generally at X, from the distal end 102 of the endoscope 100. As shown in FIG. 5B, the curved exit ports 120 result in the tips 156 of the inner tubes 154 arrive at their illustrated positions at a distance, indicated generally at Y, from the distal end 102 of the endoscope 100.

Comparing FIGS. 5A and 5B, it can be seen that the distance Y in FIG. 5B is less than the distance X in FIG. 5A. The curved exit ports 120 thus serve to move the workspace of the robotic arms 150 closer to the distal end 102 of the endoscope 100. Advantageously, this brings the workspace closer to the camera 122, irrigation/suction/drug delivery ports 124, and illumination source 126. The distance that the curved exit ports 120 move the workspace closer to the endoscope tip 102 may seem small, but this can be extremely valuable in surgical spaces where tissues surround, collapse upon and occupy the space surrounding the endoscope tip. In this environment, moving the workspace even a small distance closer to the distal end 102 of the endoscope 100 can make a great difference in visualizing the workspace.

Figure 6:
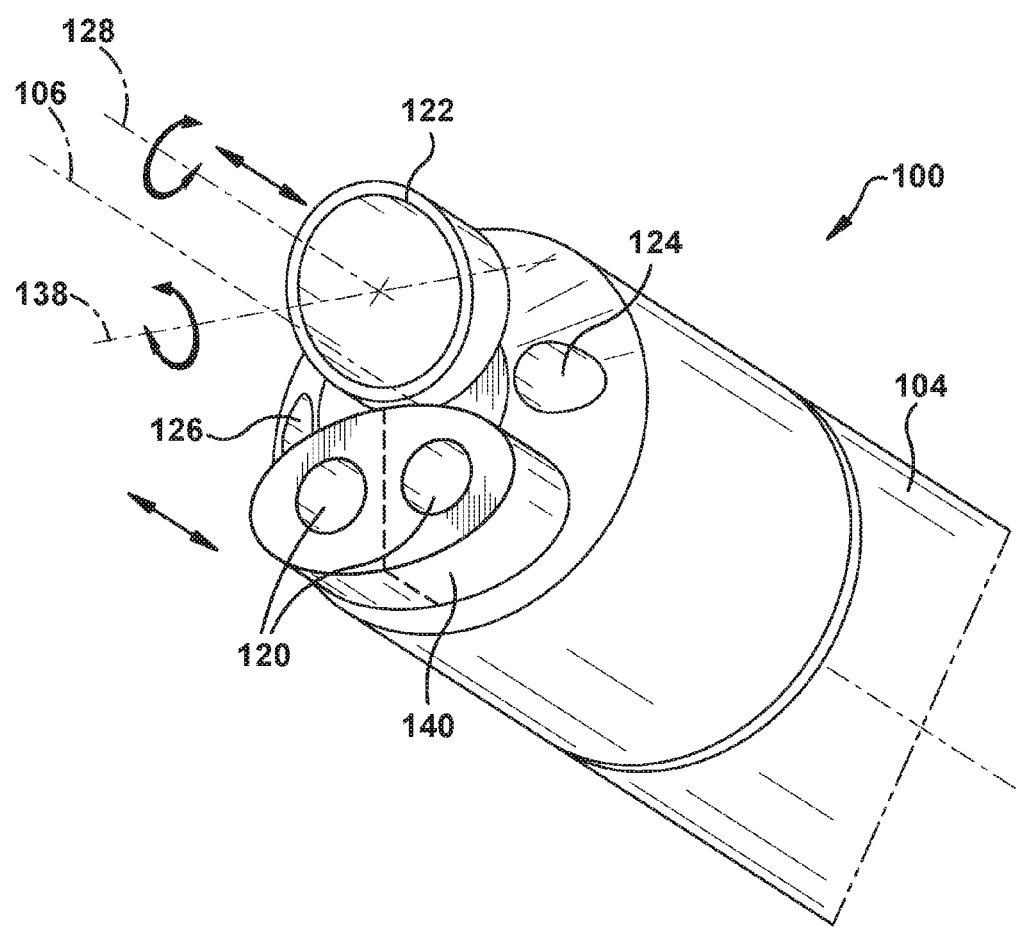
FIG. 6 is a magnified perspective view illustrating an example configuration of another portion of the robot apparatus.

The exit ports 120 can be built into the structure of the endoscope tube 104 itself, or they can be formed as an insert that is installed in the endoscope tube. This later configuration is illustrated in FIG. 6. Referring to FIG. 6, the exit ports 120 are built into an exit port insert 140. Additionally, in this example configuration, the exit port insert 140 can be configured for telescoping movement within the endoscope tube 104 parallel to the endoscope axis 106, as indicated generally by the directional arrows adjacent the exit port insert 140 in FIG. 6. In this manner, the location at which the robotic arms 150 exit the distal end 102 of the endoscope 100 can be adjusted. Advantageously, adjusting the location where the robotic arms 150 exit the endoscope tube can provide an additional degree of freedom of each robotic arm.

This axial movement could be imparted to the exit port insert 140 robotically or manually. As a further alternative, the exit port insert 140 could have a split configuration, indicated generally by the dashed lines in FIG. 6, so that the axial positions of the exit ports 120 can be adjusted individually. As another alternative, exit ports 120 could be affixed to the exterior of a commercial off-the-shelf endoscope in order to retrofit it for use with the robotic arms 150. This connection could be achieved, for instance, via a simple strap connection.

As shown in FIG. 6, the camera 122 can also be configured so that the viewpoint is positioned at an acute angle with respect to the camera axis 128, so that the field of view can encompass areas close to and including the distal end 102 endoscope 100. Additionally, the camera 122 can also be configured for telescoping movement within the endoscope tube 104 parallel to the axis 106. More specifically, the camera 122 can be configured for translational movement along a camera axis 128, as indicated generally by the linear directional arrows adjacent that axis camera in FIG. 6. Additionally, the camera 122 can also be configured for rotational movement about the camera axis 128, as indicated generally by the curved arrows extending about that axis. Furthermore, the acute angle of the camera 122 can be configured for adjustment via tilting movement about an axis 138, as indicated generally by the curved arrows extending about that axis. All of these camera motions can be controlled either robotically or manually.

This combination of translational and rotational camera movement allows for enhanced viewing capabilities in the close confines of the surgical workspace. Since the viewpoint of the camera 122 has an angled configuration, rotation of the camera changes the direction in which the camera is facing. Translational movement can move the camera closer to and away from the workspace/surgical site. Through these adjustments, the surgeon can position the camera 122 in the best possible location with respect to the workspace in order to help obtain the best possible view. Specifically, through these adjustments, the surgeon can:

Rotate the rod viewpoint axially to change the field of view and change the arms positions in that field of view.

Telescope the viewpoint to change the field of view.

Telescope the viewpoint automatically to keep the tubes in the endoscopic field of view.

Rotate the viewpoint axially to automatically keep the arms in the field of view.

Update the registration of the arms so that the motion the arms will make is independent of the field of view of the viewpoint.

Control the direction of view of the viewpoint robotically to keep the manipulators and/or the surgical site in the field of view.

Through the various optional example configurations illustrated in FIGS. 5B and 6, the location at which the robotic arms 150 exit the distal end 102 of the endoscope 100, and the field of view of the camera 122, can be adjusted. This axial movement could be imparted to the exit port insert 140 and/or camera 122 robotically or manually. Through these configurations, the position of the workspaces of the robotic arms 150 and the field of view of the camera 122 can be adjusted to cooperate with each other so that the surgeon can operate within an ideal workspace and have an ideal view of this workspace.

Concentric Tube Robotic Arm Design

Referring to FIG. 4, the robotic arms 150 are small, needle-diameter, tentacle-like robots that include multiple concentric, precurved, elastic tubes. These elastic, curved tubes are typically made of a superelastic metal alloy such as a nickel-titanium alloy ("nitinol") material. Each tube is pre-curved through a heat treatment process before being assembled concentrically with the other(s). The tubes can, individually or in combination, be rotated about the longitudinal axis of the robot and can be translated along the longitudinal axis of the robot. Through translational movement, the tubes can be retracted into one another and extended from one another.

As the precurved tubes interact with one another through relative translational and rotational movement, they cause one another to bend and twist, with the tubes collectively assuming a minimum energy conformation. The precurvature(s) of the tube(s) for a given robotic arm 150 can be selected to provide a desired workspace throughout which the tip can access. The curved shape of the distal end of the robotic arm 150 is controlled via translation and rotation of each tube at a proximal location (e.g., at its base) outside the patient. The robotic arms 150 are particularly well suited to natural orifice procedures because their small diameter and remote actuation enable them to operate in areas where bulkier actuation systems (e.g., tendons and pulleys) are not feasible. The size (i.e., diameter) of the robotic arm 150 is limited only by the size of nitinol tubes available, which can be an outer diameter of as little as 200 µm or less.

In the embodiment illustrated in FIG. 4, the robot 20 includes two concentric tube robotic arms 150. Distal ends of the robotic arms 150 carry surgical tools 130, such as the illustrated HoLEP laser fiber and grippers. The robotic arms 150 could carry alternative tools, such as surgical lasers, graspers, retractors, scissors, imaging tips (e.g., endomicroscopy, optical coherence tomography (OCT), spectroscopy), cauterization tips, ablation tips, wrists (for dexterity), curettes, morcelators, knives/scalpels, cameras, irrigation ports, and suction ports.

Each first robotic arm 150 includes two concentric tubes: an outer tube 160 and an inner tube 162. Each inner tube carries at its distal end one of the surgical tools 130. Each of the tubes has a pre-curved configuration, and this curvature can be selected so that the robot tip can "cover" a predetermined workspace in the vicinity of the distal end 102 of the endoscope 100. The tubes 160, 162 of each pair are actuatable independently of each other. Each tube 160, 162 has two degrees of freedom—translation and rotation. The robot 20 of the example configuration of FIG. 4 thus has four degrees of freedom. The degrees of freedom of the robot 20 can be re-configured by adjusting the number robotic arms 150, adjusting the number of concentric tubes in each robotic arm, or simply by configuring any particular tube for only one degree of freedom, i.e., translation only or rotation only.

In describing the unique characteristics of the concentric rube robotic arms 150 described herein, it should be noted and understood what is meant by the terms "axis" or "axial" used in conjunction with the translational and rotational movement of the tubes 160, 162 versus the axes of the tubes themselves or the robotic arms as a whole. Because the curved tubes 160, 162 are coaxial in nature, the axes of the tubes and of the robotic arms 150 themselves can be considered to be the same. The tube axes and robotic arm axis is thus centered within and follow the curved configurations of the concentric tubes. Thus, as the curved configuration of the robotic arm 150 changes, the axis of the robotic arm and the axes of the tubes themselves follow these changes in curvature.

However, in this description, reference is also made to rotation and translation and rotation of the concentric tubes 160, 162, either individually or collectively. In this description, rotation of the concentric tubes 160, 162 is meant to refer to rotation of the tubes about straight, linear portions of the tubes that extend through tube actuation modules 250 of the actuator 200 (described below), which impart both the rotational and the translational movement to the tubes. Thus, when any of the tubes 160, 162 are rotated, the portions of the tubes within the tube actuation modules 250 and the portions within the endoscope 100 rotate about this straight, linear axis, whereas curved portions of the tubes outside the endoscope move or revolve about that same axis. Similarly, when any of the tubes 160, 162 are translated, the portions of the tubes within the rube actuation modules 250 and the portions within the endoscope 100 translate along this straight, linear axis, whereas curved portions of the tubes outside the endoscope translate parallel to, but not necessarily coaxially with, that same axis. From this, it can be understood that, in a sense, translation and rotation imparted to the tubes 160, 162 can be thought of as translation along and rotation about an axis of the tube actuation modules 250, which coincides with the axes of the portions of the tubes 160, 162 held therein.

The inner tubes 162 when extended from within the outer tubes 160 will resume their precurved configurations due to their superelastic material construction. By controlling the relative translational and rotational positions of their respective tubes, the tips of the inner tubes 162, which hold the tools 130, can be maneuvered to any position within the workspace defined by the characteristics of the particular tubes. Thus, through careful selection of the tubes used to construct the robotic arms 150, their respective workspaces can be tailored to suit the particular surgical task and the physiology of the patient environment in which the task is performed.

Actuator Design
First Example Configuration

Figure 7A:
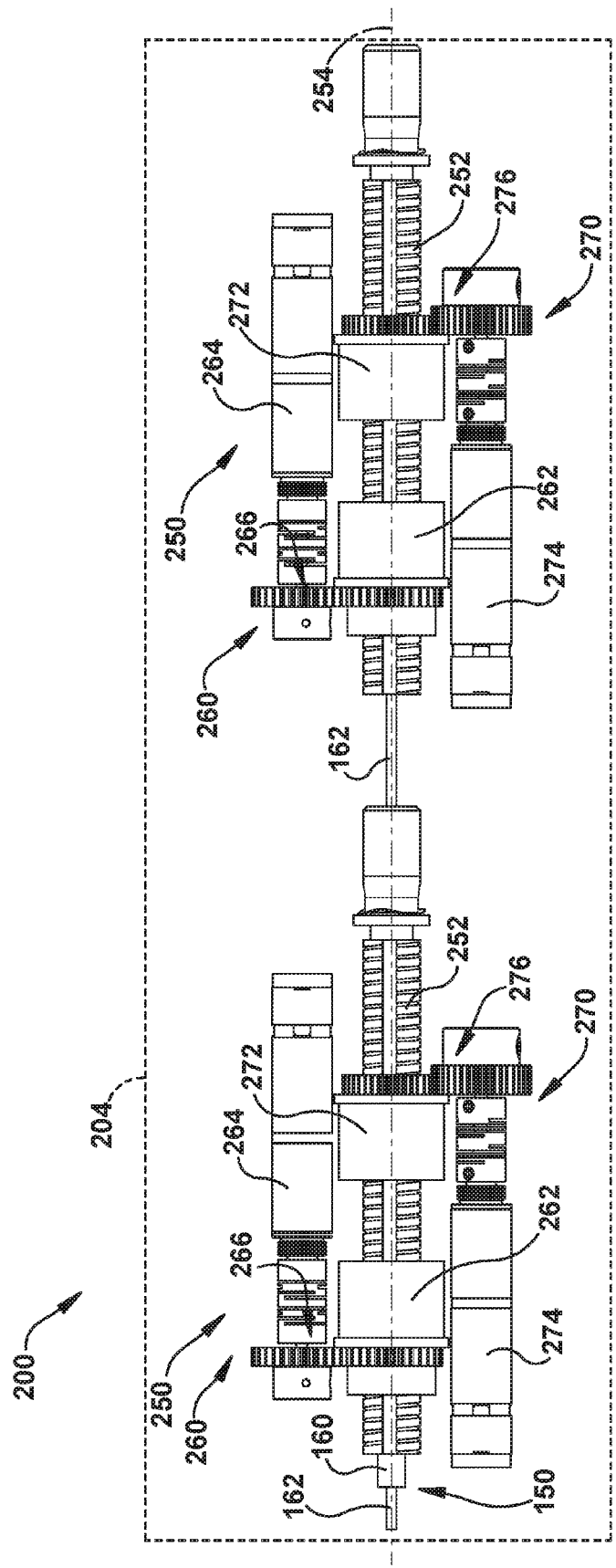
FIG. 7A is a partially schematic plan view illustrating the spatial relations and interactions of certain components of an example configuration of the robot apparatus.
Figure 7B:
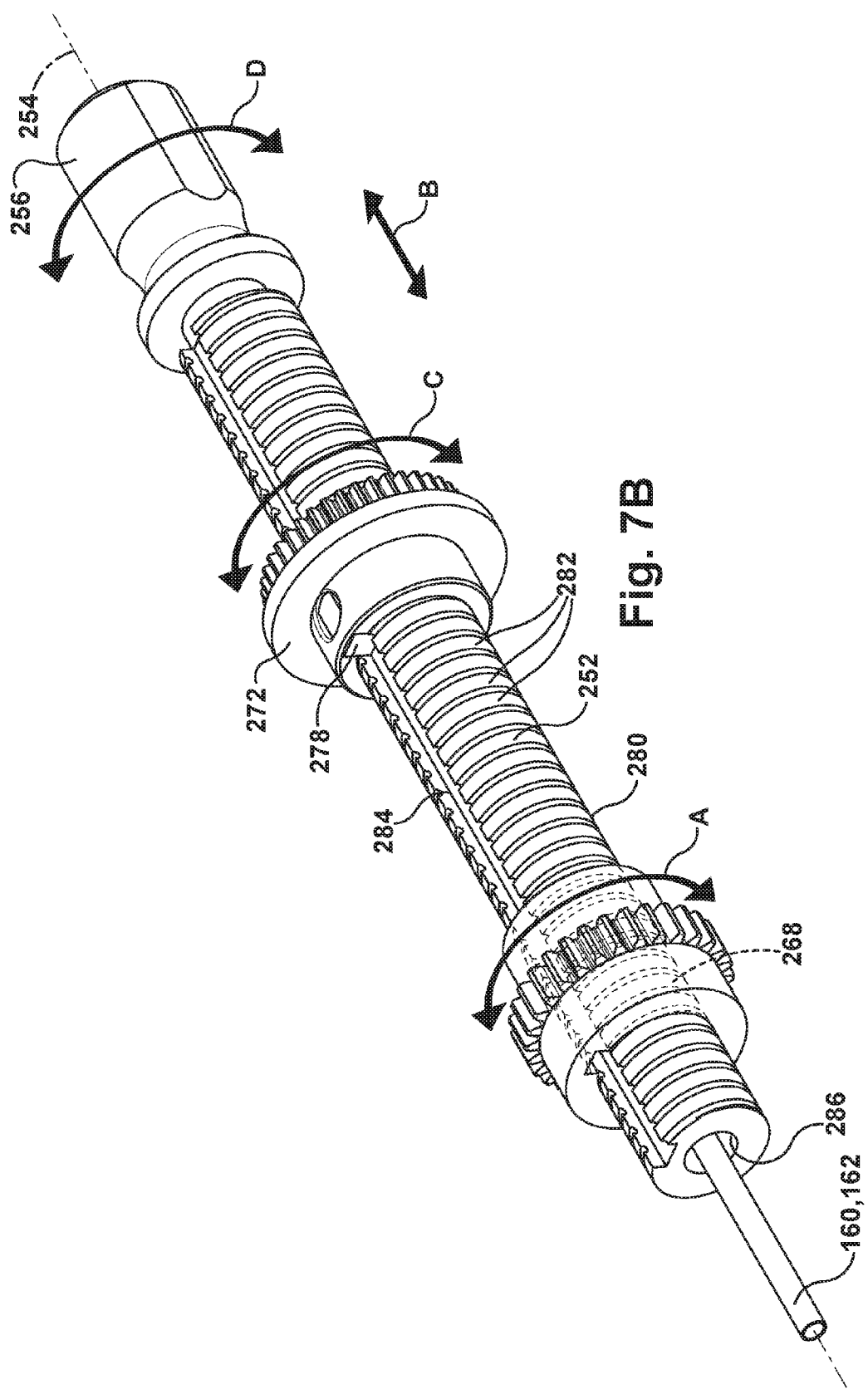
FIG. 7B is a perspective view illustrating certain components of the example configuration of FIG. 7A.

The actuator 200 controls the operation of the concentric tube robotic arms 150 by applying rotational motion, translational motion, or a combination of translational and rotational motion to each concentric tube of each arm. To facilitate this, for each concentric tube of each robotic arm 150, the actuator 200 includes a tube actuation module 250. One example configuration of the tube actuation module 250 is illustrated in FIGS. 7A and 7B. FIGS. 7A and 7B illustrate fundamental components of the tube actuation module 250 are illustrated in FIGS. 7A and 7B. In these figures, much of the structure of the tube actuation modules 250, such as support frames, housings, control components/circuitry, bushings, bearings, etc., is stripped in order to illustrate the fundamental operation of the modules. Instead, the housing and other structures that support and surround the tube actuation modules 250 are indicated generally at 204 in FIG. 7A.

In the example configuration of FIGS. 7A and 7B, each tube of a concentric tube robotic arm 150 requires an associated tube actuation module 250. For instance, the robotic arms 150 of the embodiment of FIG. 4, for example, would require two tube actuation modules 250—one associated with the outer tube 160 and one associated with the inner tube 162. This is shown in FIG. 7A. Referring to FIG. 7A, a first tube actuation module 250 (to the left as viewed in FIG. 7A) is associated with the outer tube 160, and a second tube actuation module 250 (to the right as viewed in FIG. 7A) is associated with the inner tube 162. The first and second tube actuation modules 250 can therefore be considered components of a single actuator for the concentric tube robotic arm 150.

Each tube actuation module 250 includes a tube carrier 252 to which each associated tube 160, 162 is connected. The concentric tubes 160, 162 can be connected to the tube carriers 252, for example, via a threaded compression fitting 256, via an adhesive (e.g., glued) connection, or via a cemented (e.g., epoxy) connection. In the example configuration illustrated in FIGS. 7A and 7B, the tube carriers 252 are keyed lead screws.

Those skilled in the art will appreciate that the term "lead screws" can be used to identify a specific type of threads (i.e., shape, pitch, etc.) that are particularly well-suited for providing translational axial movement in response to rotation. In this description, however, the term "lead screw" is not limited to this specific type of mechanical element. Instead, in this description, the term "lead screw" is used in the generic sense to refer to an elongated member with a threaded outer surface that is implemented to provide translational movement in response to rotation.

Additionally, the threaded configuration of the tube carriers described in the example configurations disclosed herein does not require a keyed lead screw configuration as the mechanical element used to impart translational/rotational motion of the concentric tubes. Alternative structures that can provide the concentric robotic arm assembly configuration and the associated functions disclosed herein can also be implemented as the tube carriers. For example, the tubes could be connected to a collet with a threaded outer surface that is received in a tube having a threaded interior that mates with the collet.

The actuator 200 is configured such that the lead screws 252 of each tube actuation module 250 are aligned with each other along a common axis 254. The lead screws 252 are rotatable about and translatable along this common axis 254. In some configurations (see, e.g., FIGS. 8A and 8B), these keyed lead screws 252 can have a concentric configuration in which one tube can be inserted into and passed through the other.

As shown in FIG. 7A, each lead screw 252 has associated with it a translator 260 and a rotator 270. The translator 260 includes a lead nut 262 and a motor 264 operable to impart rotation to the lead nut via drive gears 266. The rotator 270 includes a keyed collar 272 and a motor 274 that is operable to impart rotation to the keyed collar 272 via gears 276. A lead screw 252 and its associated lead nut 262 and keyed collar 272 are illustrated in FIG. 7B.

Referring to FIG. 7B, the lead screw 252 has an outer surface 280 with screw threads 282 along its length. A keyway 284 extends into the outer surface 280 and threads 282 along the length of the lead screw 252. An inner channel 286 extends through lead screw 252. It is through this channel 286 that the one or both of the outer and inner tubes 160, 162 of the concentric tube robotic arm 150 extends. For example, in the example configuration of FIG. 7A, the inner tube 162 only extends through the lead screw 252 of the right tube actuation module 250, and both the inner tube 162 and the outer tube 160 extend through the lead screw 252 of the left tube actuation module 250.

Referring back now to FIG. 7B, the lead nut 262 includes internal threads that engage and mate with the threads 282 on the lead screw. The keyed collar 272 includes no internal threads, but does include a key 278 that is seated in the collar and that is received in the keyway 284 of the lead screw 252. Both the lead nut 262 and the keyed collar 272 are supported in the structure 204 of the actuator 200 such that neither can move axially along the axis 254, but both can rotate about the axis 254.

Referring to FIG. 7B, rotation of the lead nut 262 (indicated generally by the curved arrow A) causes its internal threads 268 to engage with the external threads 282 on the lead screw 252, which urges the lead screw to undergo translational movement (indicated generally by the arrow B) along the axis 254. The keyed collar 272 does not resist translational movement of the lead screw 252 because it has no internal threads and because the keyway 284 slides along the key 278. The translator 260 translates its associated concentric tube 160, 162 by operating the translator motor 264 to impart rotation of the lead nut 262 via the gears 266 to cause translational movement of the lead screw 252 along the axis 254.

Rotation of the keyed collar 272 (indicated generally by the curved arrow C) causes the key 278 to engage the keyway 284 of the lead screw 252, which urges the lead screw to undergo rotation (indicated generally by the arrow D) about the axis 254. The rotator 270 rotates its associated concentric tube 160, 162 by operating the rotator motor 274 to impart rotation of the keyed collar 272 via the gears 276 to cause rotational movement of the lead screw 252 about the axis 254.

During operation of the rotator 270, the translator 260, particularly the lead nut 262, does not resist rotation of the lead screw. Since, however, the external threads 282 of the rotating lead screw 252 engage the internal threads 268 of the lead nut 262, rotation of the lead screw 252 about the axis 254 can also impart translation of the lead screw along the axis. Therefore, as a feature of the tube actuation module 250, the translator 260 can be operated in unison with the rotator 270 to counteract any unwanted translational movement imparted by rotation of the lead screw 252. In other words, the lead nut 262 and the keyed collar 272 are rotated in the same direction and at the same angular velocity in order to produce pure rotational movement of the lead screw 252 at that same angular velocity. Differentiation between the angular velocities of the lead nut 262 and keyed collar 272 can be implemented to impart both translation and rotation of the lead screw 252 in desired proportions.

From the above, it can be appreciated that the actuator 200 can be fit with a tube actuation module 250 for each tube of the concentric tube robotic arms 150. Since, in the example configuration of FIGS. 7A and 7B, the tube actuation modules 250 are arranged in series along the common axis 254, it will be appreciated that the actuation modules can be arranged or "stacked" in a number that corresponds to the number of tubes of the associated robotic arm 150. Thus, for example, a three tube robotic arm would require three stacked tube actuation modules 250, a four tube arm would require four stacked modules, etc.

Second Example Configuration

Figure 8B:
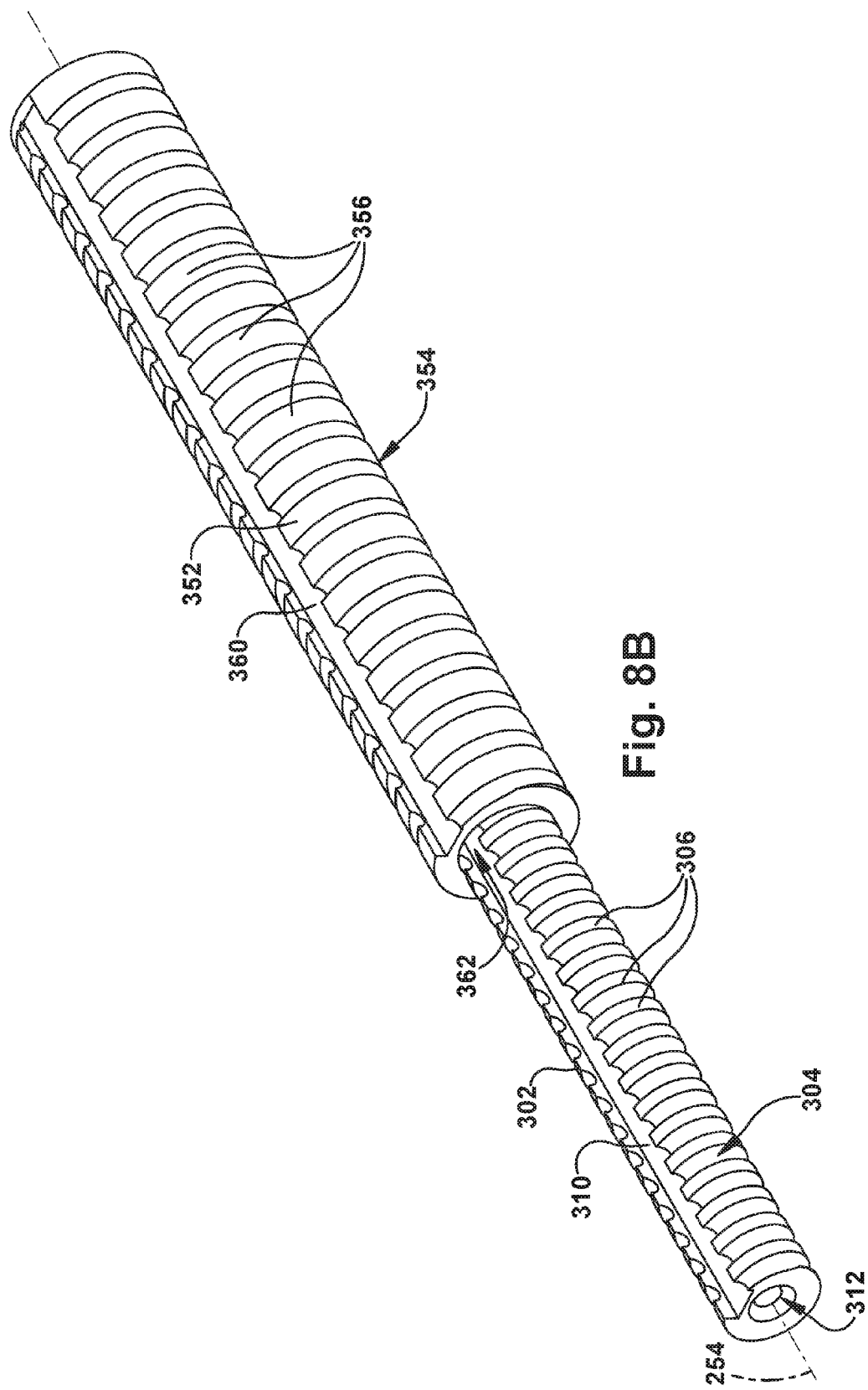
FIG. 8B is a perspective view illustrating certain components of the example configuration of FIG. 8A.

Another example configuration of the tube actuation module is illustrated in FIGS. 8A and 8B. Again, in these figures, much of the structure of the actuator 200 and the tube actuation modules, such as support housings, control components/circuitry, bushings, bearings, etc., is stripped in order to illustrate the fundamental operation of the modules.

In the example configuration of FIGS. 8A and 8B, each tube of a concentric tube robotic arm 150 requires an associated tube actuation module. The robotic arm 150 in the example configuration of FIGS. 8A and 8B is a two-tube arm and therefore requires two tube actuation modules—one associated with the outer tube 160 and one associated with the inner tube 162. In the embodiment of FIGS. 8A and 8B, the tube actuation modules function in a manner that is substantially similar or identical to the tube actuation modules illustrated in FIGS. 7A and 7B. In the example configuration of FIGS. 8A and 8B, however, the tube carriers have a concentric, nested, and telescoping configuration that allows the tube actuation modules to be arranged in a more compact manner. Instead of being spaced from each other along the common axis 254, components of the tube actuation modules can be arranged to occupy a shared space along the axis.

Referring to FIG. 8A, a first tube actuation module 300 is associated with the outer tube 160, and a second tube actuation module 350 is associated with the inner tube 162. The tube actuation module 300 includes a small diameter tube carrier in the form of a keyed lead screw 302, to which the outer tube 160 is connected. The tube actuation module 350 includes a tube carrier in the form of a large diameter keyed lead screw 352, to which the inner tube 162 is connected.

Referring to FIG. 8B, the small lead screw 302 has an outer surface 304 with screw threads 306 along its length. A keyway 310 extends into the outer surface 304 and threads 306 along the length of the lead screw 302. An inner channel 312 extends through the small lead screw 302. It is through this channel 312 that the outer and inner tubes 160, 162 of the concentric tube robotic arm 150 extend. The outer tube 160 can be fixed to the small lead screw 302, for example, via a mechanical, e.g., threaded, connection or a bonded connection, such as an epoxy bond. The inner tube 162 extends through both the outer tube 160 and the channel 312.

The large lead screw 352 has an outer surface 354 with screw threads 356 along its length. A keyway 360 extends into the outer surface 364 and threads 356 along the length of the large lead screw 352. An inner channel 362 extends through the large lead screw 352. It is through this channel 362 that the inner tube 162 of the concentric tube robotic arm 150 extends. The inner tube 162 can be fixed to the large lead screw 352, for example, via a mechanical, e.g., threaded, connection or a bonded connection, such as an epoxy bond. The inner tube 162 extends through both the outer tube 160 and the channel 362.

The lead screws have a concentric, nested configuration in which the small lead screw 302 fits within the large lead screw 352. More specifically, the outside diameter of the small lead screw 302, i.e., the major diameter of the threads 316, is selected to create a clearance with the inside diameter of the inner channel 362. The small lead screw 302 can thus move freely within the channel 362, both translationally along the axis 254 and rotationally relative to the axis.

As shown in FIG. 8A, each lead screw has associated with it a translator and a rotator. For the small lead screw 302, the translator 320 includes a lead nut 322 and a motor 324 operable to impart rotation to the lead nut via drive gears 326. Also for the small lead screw 302, the rotator 330 includes a keyed collar 332 and a motor 334 that is operable to impart rotation to the keyed collar 332 via gears 336. The lead nut 322 includes internal threads (not shown) that engage and mate with the threads 306 on the lead screw. The keyed collar 332 includes no internal threads, but does include a key (not shown) that is seated in the collar and that is received in the keyway 310 of the lead screw 302. Both the lead nut 322 and the keyed collar 332 are supported in the structure of the actuator 200 such that neither can move axially along the axis 254, but both can rotate about the axis 254.

Similarly, for the large lead screw 352, the translator 370 includes a lead nut 372 and a motor 374 operable to impart rotation to the lead nut via drive gears 376. Also for the large lead screw 352, the rotator 380 includes a keyed collar 382 and a motor 384 that is operable to impart rotation to the keyed collar 382 via gears 386. The lead nut 372 includes internal threads (not shown) that engage and mate with the threads 356 on the lead screw. The keyed collar 382 includes no internal threads, but does include a key (not shown) that is seated in the collar and that is received in the keyway 360 of the lead screw 352. Both the lead nut 372 and the keyed collar 382 are supported in the structure 204 of the actuator 200 such that neither can move axially along the axis 254, but both can rotate about the axis 254.

The tube actuation modules 300, 350 operate in a manner identical to the tube actuation module 250 of FIGS. 7A and 7B. Referring to FIG. 8A, rotation of the lead nuts 322, 372 causes their internal threads to engage with the external threads 306, 356 on their respective lead screws 302, 352, which urges the lead screw to undergo translational movement along the axis 254. The keyed collars 332, 382 do not resist translational movement of the lead screws 302, 352 because they have no internal threads and because their respective keyways 310, 360 slide along their respective keys. The translators 320, 370 thus translate their associated concentric tubes 160, 162 by operating the translator motors 324, 374 to impart rotation of the lead nuts 322, 372 via the gears 326, 376 to cause translational movement of the lead screws 302, 352 along the axis 254.

Rotation of the keyed collars 332, 382 causes their keys to engage the keyways 310, 360 of the lead screws 302, 352, which urges the lead screws to undergo rotation about the axis 254. The rotators 330, 380 thus rotate their associated concentric tubes 160, 162 by operating the rotator motors 334, 384 to impart rotation of the keyed collars 332, 382 via the gears 336, 386 to cause rotational movement of the lead screws 302, 352 about the axis 254.

Like the embodiment of FIGS. 7A and 7B, during operation of the rotators 330, 380, the translators 320, 370, particularly the lead nuts 322, 372, do not resist rotation of the lead screw. Since, however, the external threads 306, 356 of the rotating lead screws 302, 352 engage the internal threads of the lead nuts 322, 372, rotation of the lead screws 302, 352 about the axis 254 can also impart translation of the lead screws along the axis. Therefore, as a feature of the tube actuation modules 300, 350, the translators 320, 370 can be operated in unison with the rotators 330, 380 to counteract any unwanted translational movement imparted by rotation of the lead screws 302, 352. In other words, the lead nuts 322, 372 and the keyed collars 332, 382 are rotated in the same direction and at the same angular velocity in order to produce pure rotational movement of their respective lead screws 302, 352 at that same angular velocity. Differentiation between the angular velocities of the lead nuts 322, 372 and keyed collars 332, 382 can be implemented to impart both translation and rotation of their associated lead screws 302, 352 in desired proportions.

Compact Design

The small form factor of the robot 20 is owed to the compact design of the tube actuator modules. This compact, two-motor design provides two degrees of freedom for its associated tube and can be stacked with other actuators for other concentric tubes of the associated robotic arm. One subtlety of this design is that operation of the keyed collar, also causing translation due to the lead screw interaction with the lead nut, also requires actuation of the lead nut in order to provide pure rotational movement of the lead screw.

This is not trivial. In fact, this allows for the compact "stackable" design of the tube actuator modules because it eliminates the need for a unique actuator axis for each degree of freedom. Therefore, as the number of tubes increases, the number of unique motor axes also increases, and the size of the actuator increases rapidly. In example configurations, the number of unique motor axes is two, independent of the number of degrees of freedom.

As the modules are stacked axially, the motor axes are all coincident. This allows the components of the actuator 200 to be compactly housed in a relatively small package. Thus, for example, the actuator 200, housing tube actuator modules for actuating two concentric tube robotic arms, can have a package size (i.e., the generally square dimension illustrated in FIG. 2) of 2.5 inches square. The length of the actuator 200 is dependent on the number of tubes in each robot but, in the two tube configuration illustrated in FIG. 2, the housing length can be on the order of 10 inches. The size of the actuator is thus easily small enough for hand-held manipulation. Additionally, the final, assembled actuator 200 can weigh less than 2.5 pounds, including all electronics.

Tube Actuation Module Control

Figure 9A:
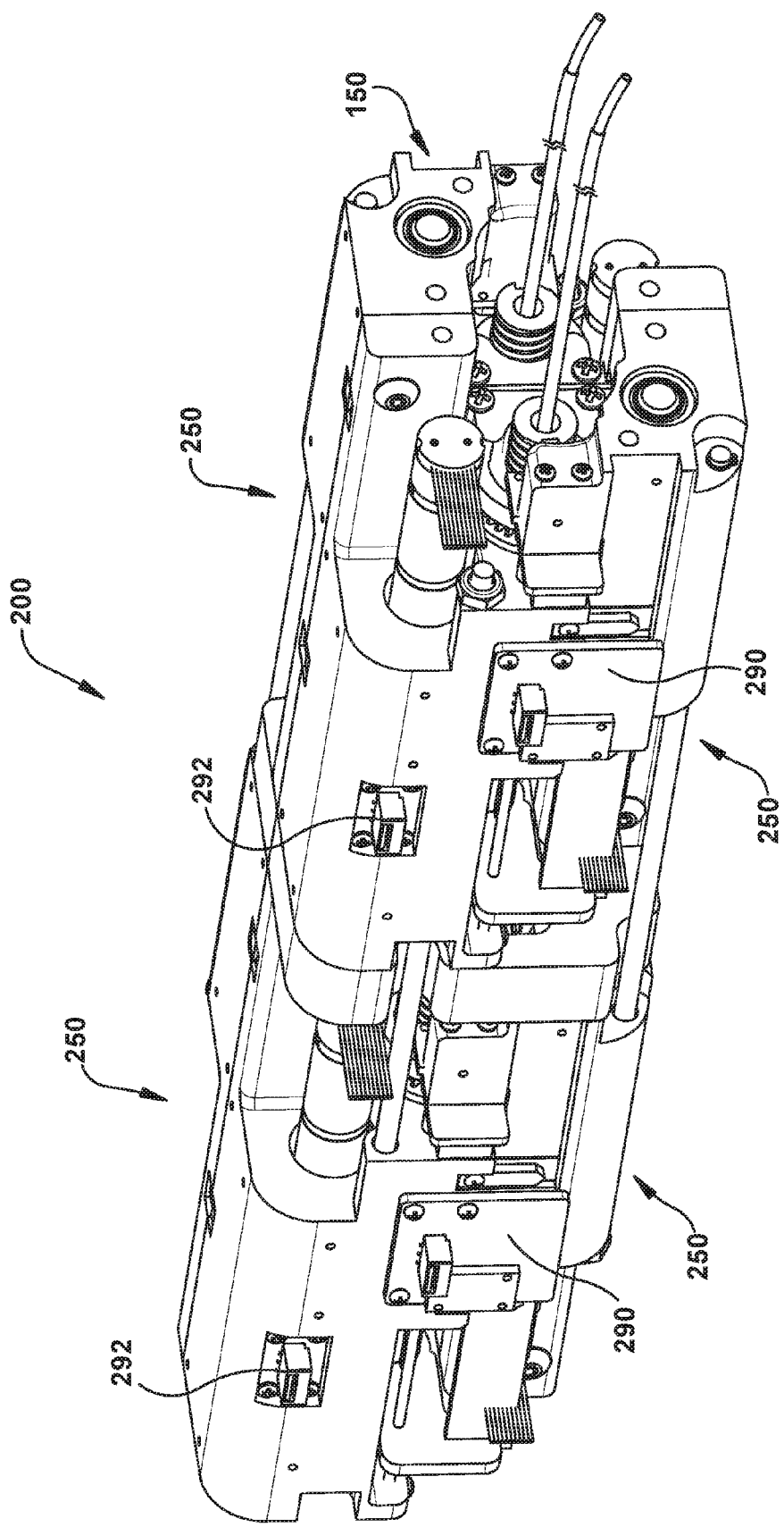

In the example configurations, the primary components of the actuator 200 are the four tube actuation modules, where each actuation module actuates a single tube. FIG. 9A illustrates the actuator 200 stripped of the outer housing to reveal the tube actuator modules and their supporting structures. The actuator 200 of FIG. 9A has the configuration of FIG. 7A and therefore illustrates tube actuator modules 250 for two concentric tube robotic arms 150, i.e., four tube actuator modules and eight motors total. It should be understood and appreciated that the control methodologies and electronics implemented to execute these methodologies will not differ for the actuator configuration of FIG. 8A and, therefore, the description of these methodologies and electronics is equally applicable to the actuator of FIG. 8A.

FDA cleared electromechanical systems require fail-safe redundant sensing mechanisms in order to guarantee safe operation of the system. The design of the robot 20 incorporates redundant sensing on the angular and linear position of the robotic arm tubes. The position of each motor is known via incremental optical encoders. This gives accurate resolution on the angular position of the motor shaft axis. Ignoring any backlash in the system, there is an exact algebraic relationship between the rotation of the motor and the position of the tube in each tube actuation module. However, should any portion of the actuation unit fail (e.g. gear teeth strip, coupling failure, etc.), then the motors' optical encoders are unaware of this. In addition to this, a system which only has optical encoders on the motors cannot characterize the backlash of the system in real-time. Therefore, the system would be unaware if the commanded motor position and the actual tube position are in significant disagreement. Another problem with only incremental encoders is that there is no mechanism to home the robot. In other words, the robot cannot realign itself between power on and power off.

The actuator 200 can be fit with a variety of magnetic sensors that provide inputs in addition to the motor position sensors to implement redundant closed loop operation of the tube actuation modules 250. For instance, in addition to the motor rotational position sensors, each tube actuation module can include a magnetic lead screw rotational position sensor (not shown) and a magnetic lead screw linear position sensor 290. Positional sensing of this type can be implemented in a variety of manners. In an example configuration, the linear position of the lead screw can be sensed magnetically with a strip magnet and a magnetic linear position sensor. The angular position of the tube can also be sensed magnetically with a multi-pole ring magnet associated with the keyed collar of the rotator assembly.

The magnetic position sensors sense actual tube position. The strip magnet sensor and ring magnet sensor can provide absolute accuracy on tube position and rotation with a high resolution, such as 10 micrometers (μm) linearly and 0.019° rotationally. Additionally, absolute linear position sensing can be obtained by sensing when the end of the strip magnet is reached. Absolute rotational position sensing can be obtained via a Hall sensor 292 for sensing a magnet embedded in the actuator motor drive gear. In this manner, the robot can "know" a home position (i.e., a zero location in translation and rotation) and therefore be able to home itself between start ups and will have a mechanism for backlash detection and built-in safety via redundant sensing. Each tube actuation module can have a total of five sensors (two motor encoders, two magnetic position sensors, and one hall sensor), for a total of 20 sensors in the robot.

Referring to FIG. 9B, the actuator 200 includes a side-mounted controller 400 for controlling the two tube actuation modules 250 on that side of the actuator. Since the tube actuation modules 250 have a stacked configuration, it will be appreciated that the controller 400 can be configured to control all of the tube actuation modules in the stack to which it is attached. Therefore, the controller 400 can be configured to control operation of the concentric tube robotic arm 150 associated with that module stack. In the example configuration of FIG. 9B, the actuator 200 would therefore include a second controller 400 for the tube actuation module stack on the rear side of the actuator as viewed in FIG. 9B. A small end portion of that second controller 400 is visible in this figure.

Although illustrated as an on-board controller in the example configuration of FIG. 9B, the controller 400 could have an alternative off-board design. For example, in one off-board configuration of the controller, the actuator 200 can be connected to a computer, such as a PC. The PC can receive commands from the surgeon and perform control calculations to determine control commands in response to the surgeon's commands. The control commands can be communicated from the PC to one or more motor controllers, which can communicate via cable(s) with the actuator 200 to command operation of the actuator motors.

The controller 400 can itself include a number of interconnected controllers purposed to control the function of the various subsystems or components of the robot 20. For example, the controller 400 can include controllers 402 for controlling the motors of the of the tube actuation modules 250 in real time. Current amplifiers 404 can supply the necessary current for controlling operation of the motors. High level kinematic computations are performed by an on-board controller 406, which can communicate with the low level motor controllers in real time. It is this controller 406 that receives inputs from the surgeon via the control interface devices 230. The controller 400 can also include additional controllers, such as video controllers, camera controllers, exit port insert controllers, etc. A reliable power source, such as a lithium-ion or lithium polymer battery pack 408 can provide power to the actuator 200. With this design, the robot 20 can have all power on board, have no external connections, and be microcontroller driven, all with an extremely small form factor.

The individual controllers implemented in the controller 400 can be any circuit element or elements that are capable of carrying out a set of programmed instructions and therefore can take a variety of forms. For example, the controllers can be central processing units (CPUs), field programmable gate arrays (FPGAs), graphics processing units (GPUs), application specific integrated circuits (ASICs), etc.

The controller 406, knowing the kinematic model for each robotic arm and being provided with precise position feedback through the sensors, can be inherently aware of the positions of the robotic arms in space and with respect to each other. This provides the unique ability to perform geometric collaborations between the robotic arms, and to situate the arms appropriately with respect to one another. This provides the robot with some unique abilities. For example:

The robotic arms can be autonomously controlled to avoid collisions with each another. This allows the robot to follow the surgeon's inputs while also preventing collisions of the arms.

The arms can be used in bipolar cautery mode, where one arm controls the positive terminal, and the other arm controls the negative terminal. The system can transition into a mode where, rather than controlling each arm independently, the surgeon controls the point at which bipolar cauterization is to take place.

The arms can also be used in a suturing mode, where the arms maintain a geometric relationship which is favorable for passing sutures. A software algorithm can maintain this geometric relationship and can be augmented by surgeon input.

The arms can recall where they have been. For example, the robot could include a feature where one arm could be commanded to position its tip where the other arm currently has its tip positioned.

One arm can generate tension on the tissue while the other cuts.

The two arms can be used in tandem for dissection (i.e., where the two arms are used to separate a tissue plane).

General bimanual manipulation of tissue.

The robotic arms could be used as tines for radiofrequency ablation. The arms could be situated relative to one another based on an understanding of the thermal spread that will be generated by each.

The two arms can cooperatively control and apply a clip to a blood vessel.

Surgical Tools and Attachment Mechanism

There are a wide variety of tools that can be delivered to the surgical worksite via the robotic arms 150. The types of tools and the combinations in which they are used is dictated by the surgical procedure being performed to a great extent, and to a lesser but relevant extent by the preferences of the surgeon performing the procedure. It can therefore be necessary to provide the ability to deliver different tools to the worksite during the same surgical procedure. It could be overly burdensome to remove the endoscope from the patient in order to swap or replace the tool. Therefore, according to one example configuration, the tools can be replaced while the endoscope remains positioned at the surgical worksite.

Figure 10A:
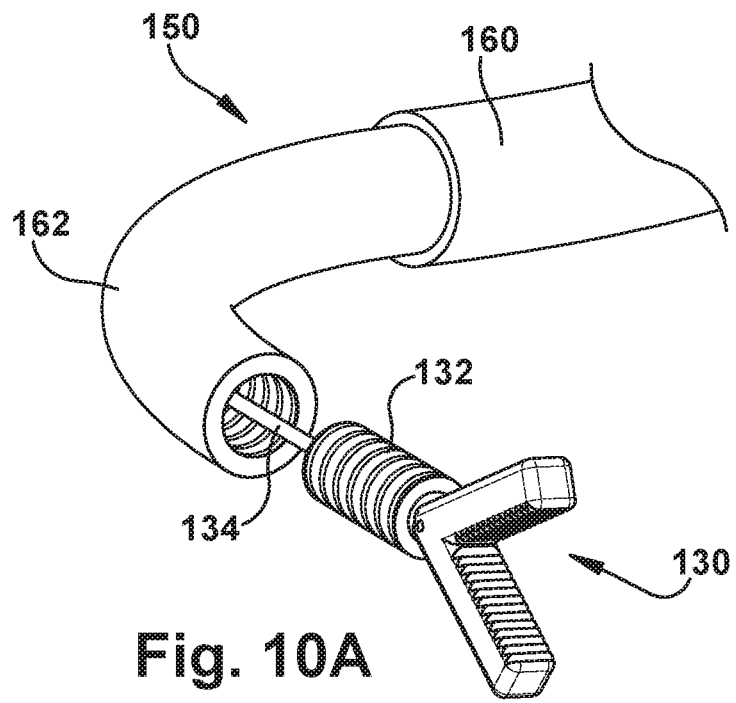
FIGS. 10A and 10B are perspective views certain components of another example configuration of the robot apparatus.
Figure 10B:
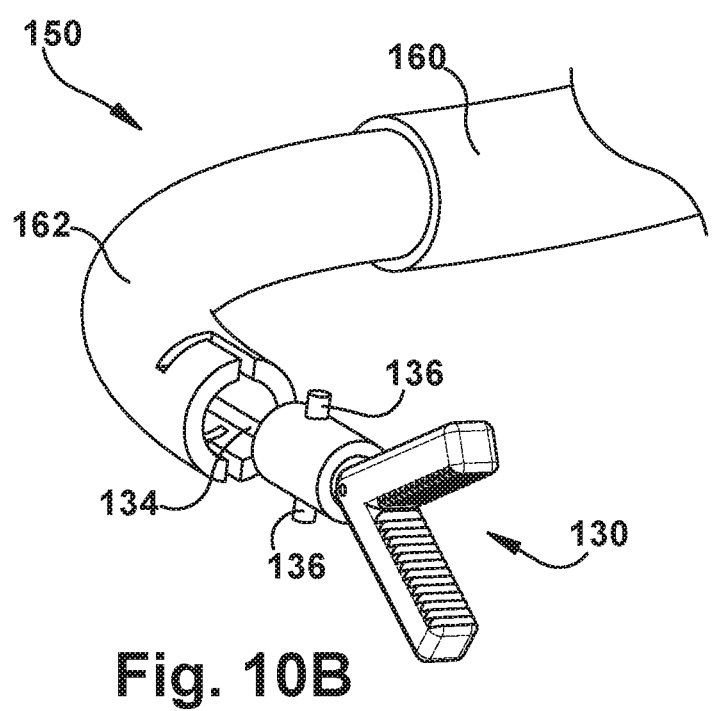

Some tools, such as laser fibers and some probes, cutters, or grippers can simply be passed through the inner lumen of the inner tube of the robotic arm 150. Other tools require attachment to the robotic arms 150. The surgical tools 130 can be attached to the robotic arms 150 in a variety of manners. For example, surgical tools 130 can be deployed through the inner channel of the concentric tube robot and attach to the distal end of the tube. Examples of this are illustrated in FIGS. 10A and 10B. In these figures, the surgical tool 130 is a gripper. The tool 130 could, however, be any of the tools described above.

In the example configurations of FIGS. 10A and 10B, the surgical tool 130 can be configured to be inserted through the tubes 160, 162 of the robotic arms 150 and attached via mechanical connections to the inner tube 162. In FIG. 10A, the tool 130 includes a threaded hub 132 that mates with a threaded portion of insert of the inner tube 162. In this example, the tool 130 is thus connected to the robotic arm 150 via a threaded, screw-in connection. To perform the rotational motion for making this threaded connection, an actuator cable 134 used to actuate the tool 130 can be rotated from a remote, proximally location on the robotic arm 150. This can allow for tool changes during a procedure without removing the robotic arm 150 from the actuator 200.

In FIG. 10B, the tool 130 includes pins 136 that project radially from a hub and mate with slots in the distal end of the inner tube 162 in a twist-lock fashion. To perform the rotational motion for making this threaded connection, an actuator cable 134 used to actuate the tool 130 can be rotated from a remote, proximally location on the robotic arm 150. This can allow for tool changes during a procedure without removing the robotic arm 150 from the actuator 200.

In an additional embodiment (not shown), the tool 130 could also be connected to the distal end of the inner tube 162 via a magnetic coupling.

Design for Sterility

Figure 11A:
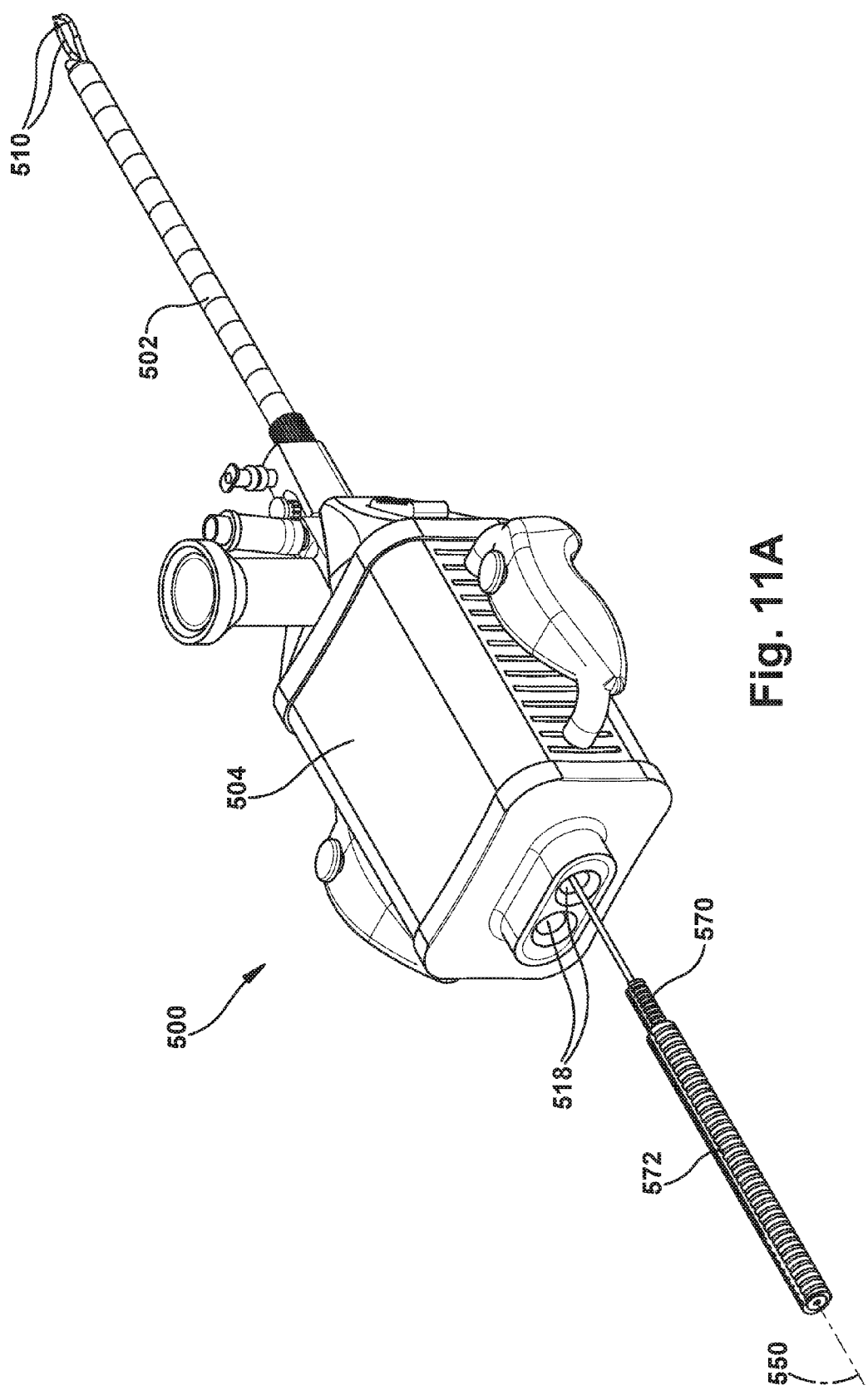

The robot can be configured for use according sterilization procedures that do not require the use of sterility bags. To achieve this, the actuator can include a non-sterile inner chamber that is surrounded by a sterile outer area that isolates the non-sterile portions from the patient environment, thus allowing the actuator to be subjected to sterilization without risking damage to the electronics or other internal components. Referring to FIGS. 11A-11D, an example configuration of the robot 500 implements a sterile design in which the endoscope 502 can be de-coupled from the actuator 504 and both the actuator and endoscope can be autoclave sterilized for repeated use. In this example configuration, the concentric tube robotic arms 510 can be single use, disposable items. As shown in FIG. 11A, the actuator 504 can have a pass-through configuration in which the concentric tube robotic arms 510 can be inserted axially from the rear of the actuator through tube insertion ports 518 that lead to tube channels 522 (see FIG. 11B) that pass through the actuator axially to the front where the concentric tubes of the robotic arms 510 exit the actuator 504 and enter the endoscope 502.

FIG. 11B is a sectional view illustrating a tube actuation module 520 for actuating one of the robotic arms 510 of the robot 500. The tube actuation module 520 can be similar in configuration to the actuation unit illustrated in FIGS. 8A and 8B. The tube actuation module 520 includes a front wall 542, a rear wall 544, and side walls 546 that extends from the front wall to the rear wall. Together, the front wall 542, rear wall 544, and side walls 546 define an outer housing 540 tube actuation module 520 that has a closed configuration defining an inner chamber 548 through which the tube channel 522 passes.

In FIG. 11B, the actuator 504 is shown in section to illustrate one of the tube actuation modules 520 for actuating one of the concentric tube robotic arms 510 of the robot 500. It will be appreciated that, in the two robotic arm configuration of the robot illustrated in FIG. 11A, the actuator 504 would include a mirror-image tube actuation module sharing the same outer housing 540 and having its own dedicated tube channel, identical to the illustrated tube channel 522 through which the second robotic arm passes.

Viewed from the aspect illustrated in FIG. 11B, the tube channel 522 extends through the inner chamber 548, from the front wall 542 to the rear wall 544. In this example configuration, the tube channel 522 includes a generally cylindrical rear section 524, a generally rectangular center section 526, and a generally cylindrical front section 528. End walls 530 and 532 of the center section 526 define an interface between the center section and the front and rear sections 524 and 528, respectively. The front, center, and rear sections 524, 526, 528, being interconnected and extending from the front wall 542 to the rear wall 544 of the housing 540, is isolated from the inner chamber 548 of the tube actuation module 520.

Figure 11D:
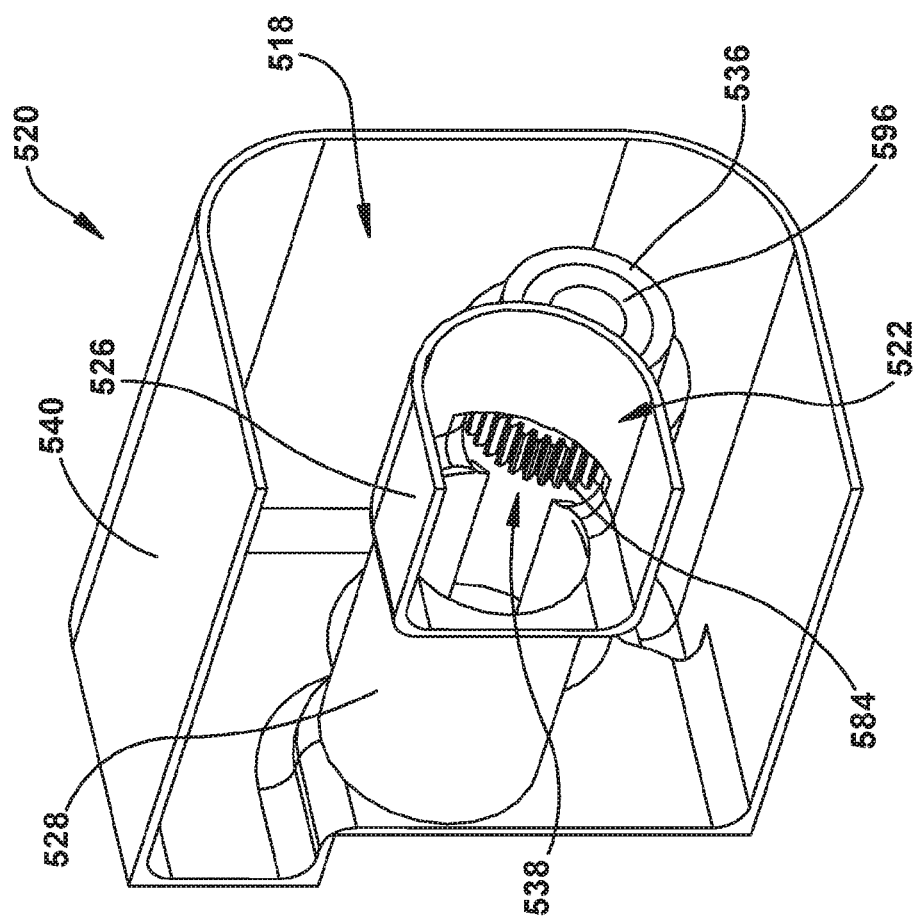

FIG. 11C is a sectional view removing a portion of the side wall 546 and viewing the illustrates the tube actuation module 520 from an aspect opposite that of FIG. 11B. Referring to FIGS. 11C and 11D, the tube channel 522 also includes generally cylindrical rear and front transmission chambers 534 and 536, respectively. The rear transmission chamber 534 has a portion that overlaps the center section 526. The front transmission chamber 536 also has a portion that overlaps the center section 526. Gear windows 538 provide fluid communication between the gear chambers 534, 536 and the center section 526, and thereby define portions of the tube channel 522.

Externally of the tube channel 522, the inner chamber 548 is a non-sterile chamber that is sealed and isolated from the tube channel. The motors (identified at 560a through 560d) for operating the robotic arms 510, and the electronics (not shown) for sensing and controlling the operation of the motors, are located in the inner chamber. The inner chamber 548 is sealed from the exterior of the tube actuation module 520 by the outer housing 540 so that sterilization of the actuator 504 does not affect these components.

The concentric tube robotic arms 510 are operated via lead screws have a concentric, nested configuration in which a small tube carrier in the form of a small keyed lead screw 570 fits within a large tube carrier in the form of a large keyed lead screw 572. The tube actuation module 520 includes a translator 580 and a rotator 590 associated with the small lead screw 570. For the small lead screw 570, the translator 580 includes a lead nut 582 and the motor 560d operable to impart rotation to the lead nut 582 via drive gears 584. Also for the small lead screw 570, the rotator 590 includes a keyed collar 592 and a motor 560c that is operable to impart rotation to the keyed collar 592 via gears 594. The lead nut 582 includes internal threads (not shown) that engage and mate with the threads on the small lead screw 570. The keyed collar 592 includes no internal threads, but does include a key (not shown) that is seated in the collar and that is received in the keyway of the small lead screw 570.

Similarly, the tube actuation module 520 includes a translator 600 and a rotator 610 associated with the large lead screw 572. for the large lead screw 572, the translator 600 includes a lead nut 602 and the motor 560a operable to impart rotation to the lead nut 602 via drive gears 604. Also for the large lead screw 572, the rotator 610 includes a keyed collar 612 and a motor 560b that is operable to impart rotation to the keyed collar 612 via gears 614. The lead nut 602 includes internal threads (not shown) that engage and mate with the threads on the large lead screw 572. The keyed collar 612 includes no internal threads, but does include a key (not shown) that is seated in the collar and that is received in the keyway of the large lead screw 572.

Both the lead nuts 582, 602 and the keyed collars 592, 612 are supported in the structure of the tube actuation module 520 such that none can move axially along the axis 550, but all can rotate about the axis 550. Specifically, the lead nuts 582, 602 and the keyed collars 592, 612 are supported by sealed bearings (see, e.g., bearings 596 in FIG. 11D) that allow for this rotation to take place across the sterile/non-sterile barrier between the tube channel 522 and the inner chamber 548. Sealed bearings 596 are known structures that permit this rotation while maintaining the seal that isolates the non-sterile inner chamber 548 from the exterior of the tube actuation module 520. For instance, bearings of this type are implemented in surgical power tools, such as drills, that can be autoclaved.

The tube actuation module 520 operates in a manner identical to the tube actuation module described above with reference 250 of FIGS. 8A and 8B. Rotation of the lead nuts 582, 602 causes their internal threads to engage with the external threads on their respective lead screws 570, 572, which urges the lead screw to undergo translational movement along the axis 550. The keyed collars 592, 612 do not resist translational movement of the lead screws 570, 572 because they have no internal threads and because their respective keyways slide along their respective keys. The translators 580, 600 thus translate their associated concentric tubes by operating the translator motors 560a, 560b to impart rotation of the lead nuts 582, 602 via the gears to cause translational movement of the lead screws 570, 572 along the axis 550.

Rotation of the keyed collars 592, 612 causes their keys to engage the keyways of the lead screws 570, 572, which urges the lead screws to undergo rotation about the axis 550. The rotators 590, 610 thus rotate their associated concentric tubes by operating the rotator motors 560c, 560d to impart rotation of the keyed collars 592, 612 via the gears to cause rotational movement of the lead screws 570, 572 about the axis 550.

Like the embodiment of FIGS. 8A and 8B, during operation of the rotators 590, 610, the translators 580, 600, particularly the lead nuts 582, 602, do not resist rotation of the lead screws 570, 572. Since, however, the external threads of the rotating lead screws 570, 572 engage the internal threads of the lead nuts 582, 602, rotation of the lead screws 570, 572 about the axis 550 can also impart translation of the lead screws along the axis. Therefore, as a feature of the tube actuation module 520, the translators 580, 600 can be operated in unison with the rotators 590, 610 to counteract any unwanted translational movement imparted by rotation of the lead screws 572, 572.

In this configuration, the motors 560a-d and the associated electronics housed inside of the inner chamber 548 are sealed against damage from the sterilization process. The exterior of the inner chamber 548, i.e., the exterior of the housing 540 and the interior of the tube channels 522, can withstand autoclaving. Therefore, the tube actuation module 520 and the actuator 504 itself can be sterilized for re-use.

Disposable Transmission

Figure 12:
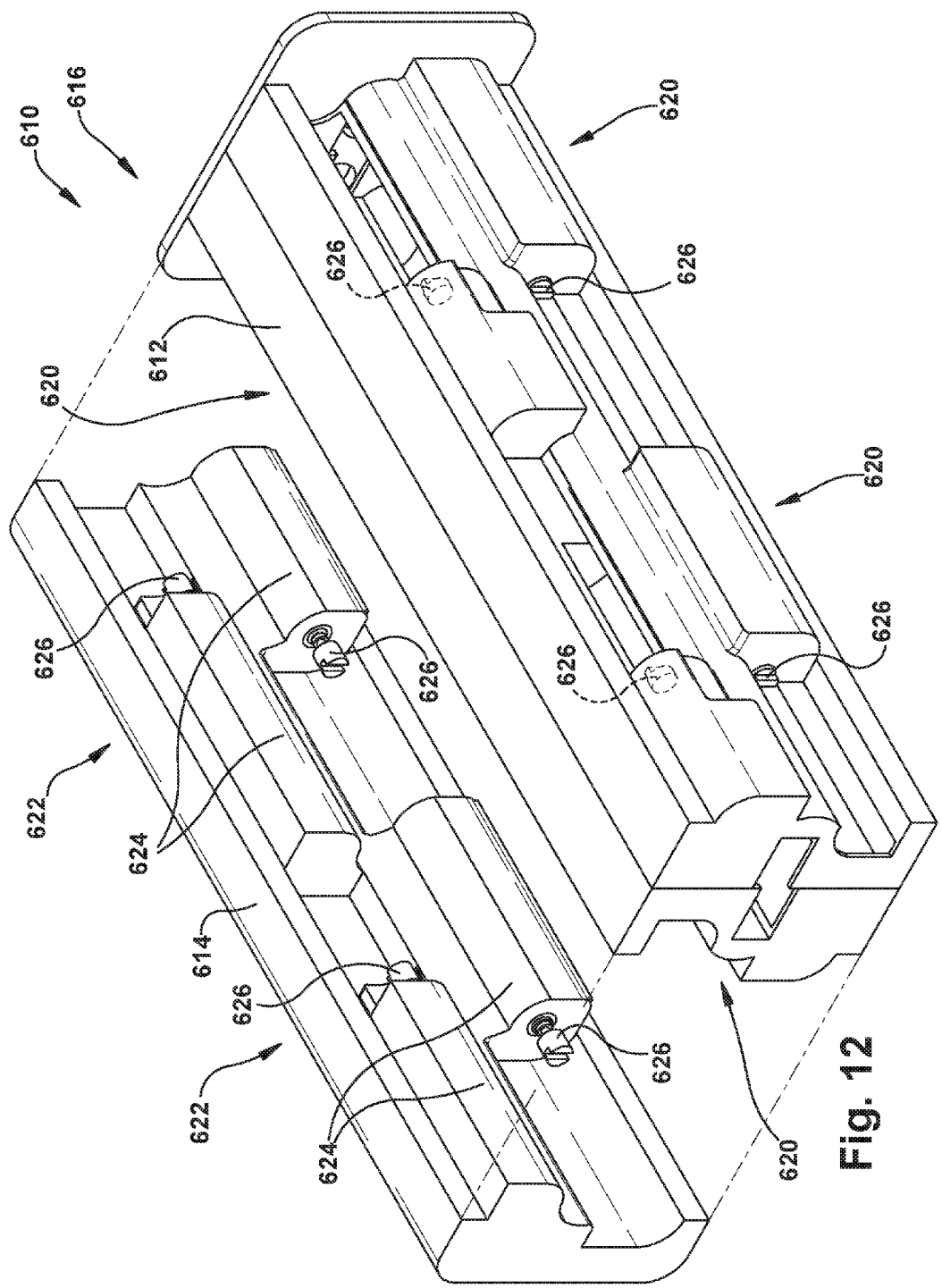
FIG. 12 is an exploded perspective view illustrating another example configuration of the robot apparatus and certain portions thereof.

Referring to FIG. 12, an example configuration of the robot 610 implements a sterile design in which includes a disposable transmission module 612 and detachable motor and electronics packs 614 to define an actuator 616. This assembly is connectable with the endoscope (not shown) in any manner similar or identical to those described above. In this configuration, the motor/electronics packs 614 are sterilization-safe components that can, for example, be autoclave sterilized. The transmission module 612, being disposable, can be shipped packaged in a sterile condition in a sterilized container. The robot 612 can thus be used in the sterile operating room environment without the need for sterile containment, such as sterilization bags.

The transmission module 612 contains within its structure the components described in previous configurations that are used to impart translational and rotational movement to the concentric tube robotic arms, with the exception of the motors, which are housed in the motor/electronics packs 614. The transmission module 612 can thus can include keyed lead screws, threaded lead nuts, and keyed collars. It can be appreciated that these components, when operated via the motor/electronics pack 614, take the form of tube actuation modules and operate accordingly. In the example configuration of FIG. 12, there are four such tube actuation modules, identified generally at 620. The manner in which these elements operate as tube actuation modules to impart rotational and translational movement of the lead screws and their associated concentric tubes of the robotic arms is described in detail with respect to the previous example tube actuation module configurations, such as those of FIGS. 7A-B and FIGS. 8A-B, and therefore is not repeated here.

The motor and electronics packs 614 can include the motors required to drive the transmission module 612 as well as the electronic components through which the robot, generally, and the motors, specifically, are controlled. The motor and electronics packs 614 can also include battery packs for powering the robot and control interface devices, e.g., handles (see FIG. 2) through which the surgeon can control operation of the robot. The transmission module 612 can also include sensors, such as linear position sensors and rotational position sensors, which can be fed to the motor and electronics packs 614 via electrical contacts or couplings that are engaged automatically when the motor and electronics packs 614 are snapped onto the transmission module 612. The motor and electronics packs 614 of the example configuration of FIG. 12 each include four motors, which correspond to controlling two degrees of freedom of two concentric tubes. The motors are thus arranged in module control packages 622, each including two motors (identified generally at 624) that correspond to the two degrees of freedom of the tube actuation module 620 with which it is associated.

When the motor/electronics packs 614 are assembled onto the transmission module 612, the module control packages 622 automatically engage and mate with their associated tube actuation modules 620. Specifically, the motor control packages 622 and tube actuation modules include drive couplings 626 that couple the outputs of the motors with the inputs of the tube actuation unit components, i.e., rotators and translators. In the example embodiment of FIG. 12, the drive couplings 626 can, for example, be Oldham couplings with mating male and female components. Alternative coupling types could be implemented. It is through these drive couplings 626 that motor rotation is imparted to the tube actuation modules 620.

The robot 610 can be configured for on-board or off-board control, as described above with respect to previous example configurations. For the on-board control implementation described above, the electronics would include those components described above with respect to the controller 400 of FIG. 9B. For an off-board control implementation, the electronics would be those necessary to pass-through the motor control signals from the external motor controllers.

Robotic Arm Installation

In the example configuration of FIGS. 11A-11D and other similarly configured actuators where the concentric tube robotic arms and their associated concentric lead screws are installed from the rear of the actuator, cooperation between the actuator and the robotic arms, especially the lead screws, is required. More specifically, the keyed lead screws have to be inserted into and through their respective tube actuation modules with their keyways aligned to receive the keys of their respective keyed collars. Since the concentric tubes connected to the lead screws are delicate surgical instruments, it is desirable to avoid having to unnecessarily manipulate or "fidget" with the lead screws to make this connection.

To accomplish this, the actuator can be configured to have a tube insertion mode in which the keyed collars of the rotators for each tube actuation unit are positioned so that the keys of those collars are aligned with each other. In this condition, the concentric lead screws can be installed in the actuator with ease, reliability, and repeatability as long as their keyways are also aligned. Therefore, the lead screws can be configured with features that help ensure proper alignment during installation of the concentric tube robotic arms.

Referring to FIG. 13A, in one example embodiment, a robotic arm assembly 650 includes concentric tubes 652, 654 that are supported by concentric tube carriers in the form of lead screws 660, 670. More specifically, an inner tube 652 is connected to an outer tube carrier in the form of an outer lead screw 660, and an outer tube 654 is connected to an inner tube carrier in the form of an inner lead screw 670. The tubes 652, 654 rotate and translate along with their respective lead screws 660, 670. The outer lead screw 660 has an inner channel 662 with a smooth surface that permits the inner lead screw 670 to rotate and slide freely therein. The inner lead screw 670 has an inner channel 672 with a smooth surface that permits the concentric tubes 652, 654 to rotate and slide freely therein.

The tulead screws 660, 670 each include an axially extending keyway 664, 674 that facilitate rotation via the rotators of their associated tuba actuation modules, as described herein above. To maintain the alignment of the keyways 664, 674 during installation, the assembly 650 includes a retention mechanism 680. In the example embodiment of FIG. 13A, the retention mechanism 680 is a spring-loaded ball retention mechanism in which the outer lead screw 660 includes a spring loaded ball bearing 682 seated within a rear collar 666 of the outer lead screw and biased toward the inner channel 662. The inner lead screw 670 includes a rear collar portion 676 that includes a receptacle 684 for receiving the spring-biased ball bearing 682.

The engagement of the ball bearing 682 in the receptacle 684 releasable locks the lead screws 660, 670 against rotation and translation relative to each other. The bearing 682 and receptacle 684 are positioned on their respective collar portions 666, 676 such that the keyways 664, 674 of the lead screws 660, 670 are aligned with each other when the retention mechanism 680 is in this locking condition. The receptacle 684 can have a tapered or chamfered edge so that relative rotation and/or translation between the lead screws 660, 670 overcomes the spring bias of the ball bearing 682 and releases the lead screws.

To use the robotic arm assembly 650, the lead screws 660, 670 and their associated tubes 652, 654 are assembled concentrically with the outer tube 652 receiving the inner tube 654 and the outer lead screw 660 receiving the inner lead screw 670. The keyways 664, 674 are aligned with each other and the inner lead screw 670 is urged into the outer lead screw 660 until the retention mechanism locks the screws together. The robotic arm assembly 650 can them be inserted into the actuator of the robot (see, e.g., FIG. 11A). When the lead screws 660, 670 are installed, their aligned keyways 664, 674 can be aligned with the keys of the keyed collars of the actuator. The actuator, having been placed in a tube insertion mode, aligns the keys to facilitate the installation of the lead screws 660, 670. The actuator can also include indicia that alerts the surgeon/user how to orient the keyways 664, 674 during so that they "hit" the keys. Once installed, the tube actuation module can operate to translate and/or rotate the lead screws 660, 670 in order to release the retention mechanism 680. The robotic arm assembly 650 is then installed and ready for use.

Referring to FIG. 13B, in an alternative example configuration, the lead screws 660, 670 can include a magnetic retention mechanism 690. In this configuration, the outer lead screw 660 can include an internal key 692 that is received in the keyway 674 of the inner lead screw 670 to maintain the relative rotational and translational positions of the lead screws 660, 670. This maintains the alignment of the keyways 664, 674. The retention mechanism 690 also includes magnetic structures 694, 696 mounted to the outer and inner lead screws 660, 670, respectively, that maintains this alignment during installation of the robotic arm assembly 650.

Safety Systems

The robot 20 can have several safety features facilitated through the design and configuration details described above. Some of these features are described in the following paragraphs.

Follow-the-Leader Retraction

The concentric tube robotic arms can be retracted in a "follow-the-leader" manner. In other words, the tip of the arm will be retracted along the exact same curve as the arms. This can be thought of as moving like a snake in which the tip and the body follow the same path of retraction into the endoscope. This can be accomplished in both a purely mechanical and a robotic manner. The controller knows the position of the tip of the robotic arm and also the path that the tip took to get to that position. The controller can thus reverse this path during retraction.

Endoscope Ejection

The endoscope can be "ejected" from the remainder of the robot as described above in reference to the example embodiment of FIGS. 4A and 4B. During surgery, the endoscope can be removed and remain at the surgical site. This can be beneficial, for example, where the actuator needs to be removed or replaced. In this instance, the robotic arms can be retracted into the endoscope; the endoscope can be detached from the actuator; and the actuator, along with the robotic arms, can be removed. A new actuator/robotic arms combination can then be fixed to the endoscope and the surgery can proceed. This can also be beneficial in the event of a medical emergency or a power failure. In a power failure situation, removal of the actuator can allow the procedure to be continued manually, especially where the endoscope is a conventional endoscope and includes an eyepiece for manual use (see. E.g., FIGS. 3A and 3B).

System Monitoring

The robot can include a system monitoring software module. This software module can identify the nominal dynamic parameters of each robot axis (i.e. damping ratio, the natural frequency, etc.). These parameters can be identified initially at the factory prior to shipping the actuator to the customer. Subsequently, these parameters can be continually monitored on-board to detect any unexpected changes that could indicate wear or damage to the actuator that may require maintenance. The robot can alert the surgeon/user to any potential wear/damage and can indicate to the user that maintenance is required. This real-time system monitoring can enable the robot to predict and alert the surgeon/user to problems before they occur and address them through routine maintenance.

Torque Monitoring

The robot can also include a torque monitoring software module for monitoring the torque output of each motor. The torque can be sensed by measuring the electrical current running through each motor. If any unexpected spike in torque is sensed, it indicates higher than expected motor effort, which could be caused by jamming of one robot axis via mechanical damage or from a foreign body. Conversely, if a sudden unexpected drop in torque occurs, this could indicate stripped gear teeth or other damage to the robot that decouples the load from the motor. If either of these conditions occurs, the robot can provide an alert to the surgeon/user and robot operation can be halted.

Real-Time Tube Model Computation

The kinematic model for concentric tube robots can be computed in real time on the onboard controller or an external controller/PC. The kinematic model allows for precise conversion of surgeon commands, input via the control interface devices, to concentric tube arm motions. While fast model computation is within the capabilities of the system, it is important to implement the software within a real-time framework so that the time consumed in each iteration is precisely determined. Without this real-time computation, there would be a delay or lag between surgeon inputs and robot response, which cannot be tolerated.

The foregoing has described certain aspects of example configurations of the robot apparatus and certain components of the robot apparatus. While specific example configurations of the robot have been described, those skilled in the art will perceive improvements, changes, and modifications can be made without departing from the spirit and scope of the invention. For example, the keyed designs of the rotators described in the example configurations disclosed herein place the keyways on the lead screw and the keys on the collar so that rotation of the collar imparts rotation to the lead screw. Those skilled in the art will appreciate that these elements could be reversed, i.e., the "key" being in the form of a longitudinally extending spline on the lead screw that passes through and engages a keyway on the collar, while maintaining the same function.

Additionally, those skilled in the art will appreciate that certain components of the robot apparatus that have been illustrated as being implemented in certain ones of the example configurations of the robot apparatus can be implemented in any of the example configurations in any combination. Accordingly, the foregoing descriptions of the example configurations are provided for the purpose of illustration only and not for the purpose of limitation. Such improvements, changes, and modifications are within the skill of the art and are intended to be covered by the appended claims.

We claim:

1. A robotic surgical apparatus comprising:
a robotic arm comprising at least two tubes having a nested, concentric configuration with an inner tube positioned in an outer tube, wherein the tubes are constructed of a superelastic material, have pre-curved configurations, and are configured to deliver surgical therapy via a distal tip of the robotic arm, wherein the position and orientation of the distal tip is effectuated through individual or collective rotation of the tubes about a tube axis and/or individual or collective translation of the tubes along the tube axis;
wherein the robotic arm further comprises a first tube carrier connected to the outer tube and a second tube carrier connected to the inner tube, wherein each of the first and second tube carriers comprise externally threaded structures arranged coaxially with each other along the tube axis; and
an actuator for actuating the robotic arm, wherein the actuator is configured to receive the robotic arm via a tube insertion interface into which the robotic arm can be inserted, wherein the actuator comprises:
a first translator comprising an internally threaded structure through which the first tube carrier extends, wherein internal threads of the first translator engage external threads of the first tube carrier;
a motor for imparting rotation to the first translator to produce translational movement of the first tube carrier and the outer tube along the tube axis;
a second translator comprising an internally threaded structure through which the second tube carrier extends, wherein internal threads of the second translator engage external threads of the second tube carrier;
a motor for imparting rotation to the second translator to produce translational movement of the second tube carrier and the inner tube along the tube axis;
a first collar through which the first tube carrier extends, the first collar and first tube carrier comprising a keyed mechanism configured such that rotation of the first collar imparts rotational movement of the first tube carrier; and
a motor for imparting rotation to the first collar to produce rotational movement of the first tube carrier and the outer tube about the tube axis;
a second collar through which the second tube carrier extends, the second collar and second tube carrier comprising a keyed mechanism configured such that rotation of the second collar imparts rotational movement of the second tube carrier; and
a motor for imparting rotation to the second collar to produce rotational movement of the second tube carrier and the inner tube about the tube axis.

2. The robotic surgical apparatus recited in claim 1, wherein the tube insertion interface is positioned on a rear portion of the actuator, wherein the actuator has a pass-through configuration in which the robotic arm passes axially through the actuator and exits a front portion of the actuator.

3. The robotic surgical apparatus recited in claim 1, further comprising an endoscope having a tip configured to be positioned at a surgical site in the patient, the apparatus being operable to deliver the robotic arm through the endoscope to the surgical site.

4. The robotic surgical apparatus recited in claim 3, further comprising a quick release mechanism for detaching the endoscope.

5. The robotic surgical apparatus recited in claim 3, wherein the endoscope comprises a camera having a viewpoint that is angled relative to a longitudinal axis of the endoscope, the viewpoint being at least one of rotatable, translatable, and angularly adjustable relative to the endoscope tip in order to adjust the field of view.

6. The robotic surgical apparatus recited in claim 3, wherein the endoscope comprises a distally located exit port through which the robotic arm extends, the exit port being translatable relative to the endoscope tip in order to adjust the exit location of the robotic arm.

7. The robotic surgical apparatus recited in claim 3, wherein the apparatus imparts motion to two robotic arms, and wherein the endoscope comprises a distally located exit port insert through which the robotic arms extend, the exit port insert being translatable relative to the endoscope tip individually in order to adjust the exit locations of the robotic arms individually.

8. The robotic surgical apparatus recited in claim 3, wherein the endoscope comprises a distally located exit port through which the robotic arm extends, the exit port having a curved configuration that permits the robotic arm to exit the exit port at an angle or along a curved trajectory relative to the endoscope axis.

9. The robotic surgical apparatus recited in claim 1, further comprising a control unit including one or more motor controllers for controlling operation of the motors, and a controller configured to communicate and control operation of the motor controllers, wherein the controller is configured to perform kinematic computations to transform user inputs into motor controller commands.

10. The robotic surgical apparatus recited in claim 1, further comprising a controller for controlling operation of the motors to impart translation, rotation, or both translation and rotation to the tube carriers and their associated tubes, wherein to produce pure rotational movement of the carriers, the controller is programmed to operate the electric motors to impart rotation of both the translators and the rotators at the same absolute angular velocity.

11. The robotic surgical apparatus recited in claim 1, wherein the first and second tube carriers are tubular, each including a longitudinally extending central channel, the first tube carrier being dimensioned to fit within the central channel of the second tube carrier in a concentric and telescoping manner, and wherein the first and second tube carriers are rotatable and translatable relative to each other.

12. The robotic surgical apparatus recited in claim 1, wherein the robotic arm includes a retention mechanism for maintaining the relative positions of the first and second tube carriers during insertion of the robotic arm into the actuator.

13. The robotic surgical apparatus recited in claim 12, wherein the retention mechanism comprises a spring loaded ball and detent mechanism or a magnetic mechanism.

14. The robotic surgical apparatus recited in claim 1, wherein the actuator has a tube installation mode in which tube actuation components are positioned automatically to align with engagement features of the tube carriers when the robotic arm is inserted through the tube insertion interface.

15. The robotic surgical apparatus recited in claim 14, wherein the actuator is configured to enter the tube installation mode automatically in response to insertion of the robotic arm.

16. The robotic surgical apparatus recited in claim 1, wherein the actuator has a tube retraction mode in which the inner and outer tubes are retracted from the patient automatically, the apparatus being configured to retract the inner and outer tubes along the same path along which the tubes were delivered into the patient.

17. The robotic surgical apparatus recited in claim 1, wherein the actuator has a tube exchange mode in which the inner and outer tubes are retracted to a position where at least the inner tube can be removed from the actuator and replaced with a different inner tube.

18. The robotic surgical apparatus recited in claim 1, wherein the inner tube has a distal tip configured to support surgical tools, wherein the surgical tools can be delivered to the tip through an inner lumen of the inner tube, the tip of the inner tube and the surgical tool comprising portions that cooperate to form a connection mechanism for connecting the surgical tool to the tip of the inner tube, and wherein the surgical tool can be manipulated to engage and disengage the connection mechanism remotely by manipulating a tool apparatus member that is connected to the tool and extends through the inner lumen of the inner tube.

19. The robotic surgical apparatus recited in claim 18, wherein the connection mechanism comprises a threaded connection or a pin-and-slot locking mechanism.

20. The robotic surgical apparatus recited in claim 1, wherein the actuator comprises a housing comprising an inner chamber and a tube channel that extends through the inner chamber, the tube channel being isolated from the inner chamber, wherein motors for actuating the robotic arm, and electronic components associated with the motors are housed in the inner housing, and wherein the robotic arm extend through the tube channel.

21. The robotic surgical apparatus recited in claim 20, wherein the motors and electronic components are sealed in the inner chamber, the seal of the inner chamber being sufficiently gas-tight to permit the apparatus to be sterilized.

22. The robotic surgical apparatus recited in claim 20, further comprising sealed bearing structures through which motor shafts extend from the inner chamber into the tube channel, the sealed bearing structures maintaining the seal between the inner chamber and the tube channel to a level sufficient to permit sterilization of the actuator.

23. The robotic surgical apparatus recited in claim 1, wherein the actuator comprises:
  a disposable transmission assembly for receiving the robotic arm and imparting translational and rotational movement to the robotic arm; and
  at least one motor and electronics pack that is connectable to the transmission assembly and is operable to provide motive force to the disposable transmission assembly for imparting the translational and rotational movement to the robotic arm.

24. The robotic surgical apparatus recited in claim 23, wherein the at least one motor and electronics pack comprises controller components for controlling operation of the motors in order to control actuation of the robotic arm.

* * * * *